United States Patent
Bishop et al.

(10) Patent No.: US 8,404,636 B2
(45) Date of Patent: Mar. 26, 2013

(54) TARGETED DELIVERY OF ANTIMICROBIAL AGENTS

(75) Inventors: Barney Bishop, Annandale, VA (US); Monique van Hoek, Centreville, VA (US); Keith M. Davies, Haymarket, VA (US)

(73) Assignee: George Mason Intellectual Properties, Inc., Fairfax, VA (US)

( * ) Notice: Subject to any disclaimer, the term of this patent is extended or adjusted under 35 U.S.C. 154(b) by 556 days.

(21) Appl. No.: 12/502,420

(22) Filed: Jul. 14, 2009

(65) Prior Publication Data

US 2010/0022750 A1    Jan. 28, 2010

Related U.S. Application Data

(60) Provisional application No. 61/081,557, filed on Jul. 17, 2008.

(51) Int. Cl.
*A61K 38/08*    (2006.01)
(52) U.S. Cl. .................... 514/2.3; 514/21.6
(58) Field of Classification Search .......... None
See application file for complete search history.

(56) References Cited

FOREIGN PATENT DOCUMENTS

WO    WO 2007/126392    * 11/2007

OTHER PUBLICATIONS

Brogden "Antimicrobial peptides: pore formers or metabolic inhibitors in bacteria," *Nat. Rev. Microbiol.*, 2005,3(3):238-250.

Lee et al., "Structure-antimicrobial activity relationship between pleurocidin and its enantiomer," *Exp. Mol. Med.*, 2008, 40(4):370-376.
Tossi et al. "Amphipathic, alpha-helical antimicrobial peptides," *Biopolymers*, 2000, 55(1):4-30.
van 't Hof et al. "Antimicrobial peptides: properties and applicability," *Biol. Chem.*, 2001, 382(4):597-619.
Vunnam et al. "Synthesis and study of normal, enantio, retro, and retroenantio isomers of cecropin A-melittin hybrids, their end group effects and selective enzyme inactivation," *J. Pept. Res.*, 1998, 51(1):38-44.
Wade et al. "All-D amino acid-containing channel-forming antibiotic peptides," *Proc. Natl. Acad. Sci. USA*, 1990, 87(12):4761-4765.
Zhao et al., "Identification and characterization of novel reptile cathelicidins from elapid snakes," *Peptides*, 2008, 29(10):1685-1691.

* cited by examiner

*Primary Examiner* — Christina Bradley
(74) *Attorney, Agent, or Firm* — Fish & Richardson P.C.

(57) ABSTRACT

A cationic antimicrobial peptide (CAMP) conjugate is disclosed. The CAMP conjugate may be made by identifying a suitable carrier peptide; identifying a suitable antimicrobial agent; creating a conjugate by conjugating the peptide with the antimicrobial agent; and evaluating and refining the conjugate. The peptide may be short peptide based on the sequence of a CAMP, such as human β-defensin-3. The peptide can be directly connected to the antimicrobial agent or through a linker segment. The antimicrobial agent may be connected to the peptide or the linker segment through stable or cleavable bonding. The peptide may carry and facilitate the delivery of the conjugated antimicrobial agent to a microbe.

18 Claims, 21 Drawing Sheets

```
                                    S205
         ┌─────────────────────────────────────────┐
         │      Identify a suitable carrier peptide │
         └─────────────────────────────────────────┘
                           │
                           ▼         S210
         ┌─────────────────────────────────────────┐
         │    Identify a suitable antimicrobial agent │
         └─────────────────────────────────────────┘
                           │
                           ▼         S215
         ┌─────────────────────────────────────────┐
         │ Create a conjugate by conjugating the peptide with the
         │ antimicrobial agent, wherein the peptide a short peptide
         │ based on the sequence of a beta-defensin or a CAMP;
         │ directly connected to the antimicrobial agent or through a
         │ linker segment, the antimicrobial agent being connected to
         │ the peptide or the linker segment through stable or
         │ cleavable bonding; and carries and facilitates the delivery
         │ of the conjugated antimicrobial agent to a microbe
         └─────────────────────────────────────────┘
                           │
                           ▼         S220
         ┌─────────────────────────────────────────┐
         │        Evaluate and refine the conjugate │
         └─────────────────────────────────────────┘
```

FIG. 2

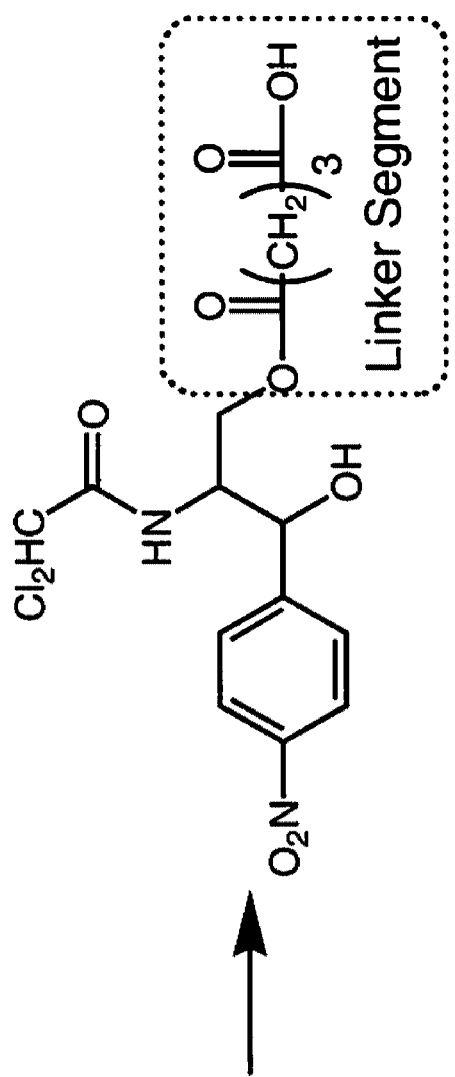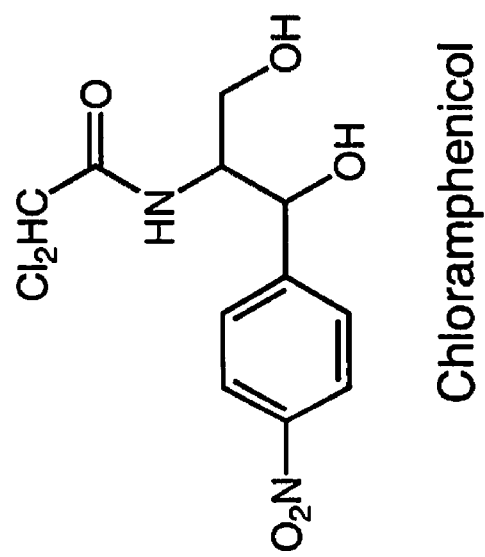
FIG. 11

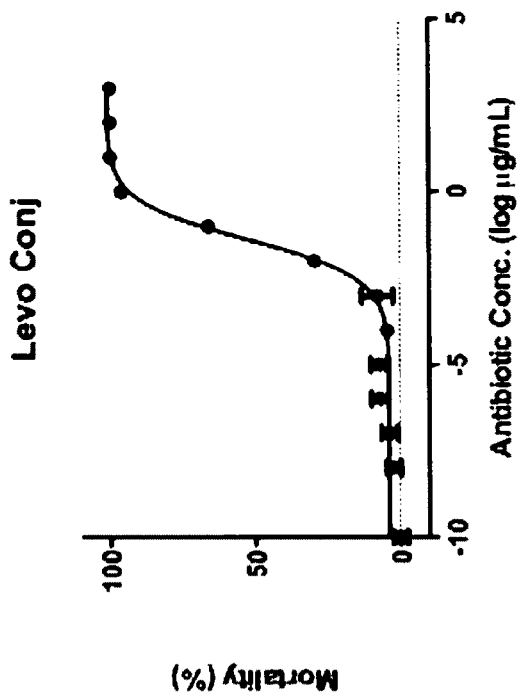
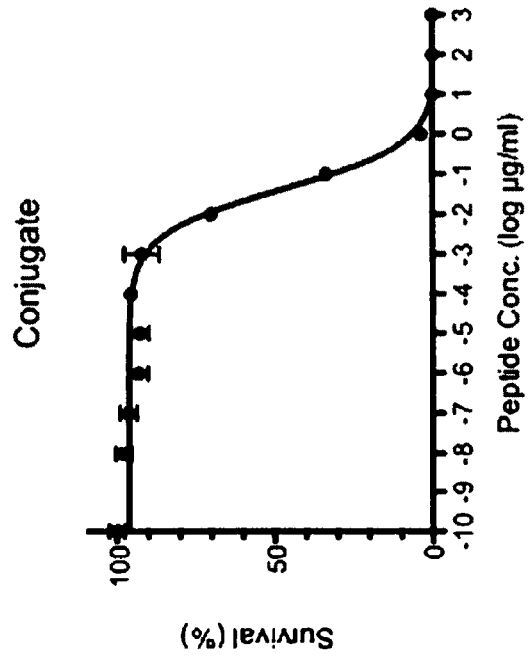
FIG. 16

A.
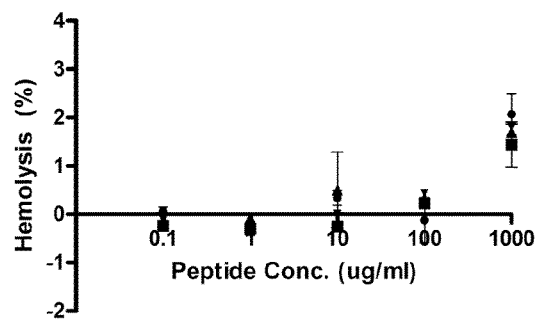
B.
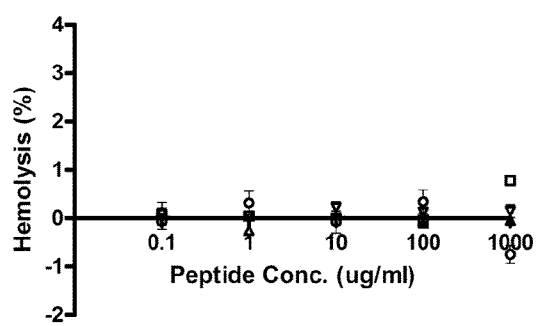
FIG. 21

TARGETED DELIVERY OF ANTIMICROBIAL AGENTS

CROSS REFERENCE TO RELATED APPLICATIONS

The present application claims the benefit of provisional patent application Ser. No. 61/081,557 to Bishop, filed on Jul. 17, 2008, entitled "Targeted Delivery of Antimicrobial Agents," which is hereby incorporated by reference.

BACKGROUND OF THE INVENTION

Before the discovery of antibiotics, community-acquired infections were a major threat to the health and welfare of people in the United States, and they continue to be a major problem in developing countries. However, soon after the discovery of penicillin and wide spread access to antibiotics in the 1940's, bacteria began to develop varied degrees of resistance to these drugs. While new drugs have been introduced since the discovery of penicillin, the majority of them are the result of varied combinations of substituents on one of about 9 molecular scaffolds. There should be no surprise that the number of microbes developing resistance is growing rapidly, and that their resistance mechanisms are becoming more sophisticated. For example, antibiotic resistance was initially a problem associated with nosocomial infections. But now, there has been an increase in occurrences in community acquired cases. Antibiotic resistance appears to now threaten the utility of "last resort" drugs, such as vancomycin, the drug of choice for treating methicilin- and multidrug-resistant *Staphylococcus aureus* infections. The problem of antibiotic resistance is further complicated by the threat of bioterrorism, and the potential use of pathogens that have been intentionally altered in order to enhance their resistance to antibiotics and to enhance their virulence or lethality.

Today, gastrointestinal pathogens continue to present a threat to the health of Americans and people worldwide, particularly children in developing nations. While many of these illnesses can be treated, several of them (such as shigellosis and cholera) can have fatal consequences if untreated. There is an urgent need to develop new therapeutics to better address this threat. It has been estimated that as many as about 325,000 Americans are hospitalized and up to about 5,000 die per year due to food-borne pathogens and the resulting gastrointestinal (GI) infections.

The *Shigella* family of bacteria is a particularly virulent group of gastrointestinal pathogens that are spread by contaminated food or water. Infection can occur with as few as 10 ingested cells. According to the Centers for Disease Control, as many at 18,000 cases of shigellosis are reported in the United States each year, and it is estimated that the actual number of cases in the United States is closer to 300,000 per year. Shigellosis is a greater problem in developing countries, accounting for about 99% of the estimated 165 million cases worldwide each year. Children in developing countries are particularly susceptible to shigellosis, with children under five accounting for nearly 60% of the ~1.1 million deaths each year.

In 1994, there was an outbreak of *Salmonella enteriditis* in the United States that affected approximately 224,000 people. This outbreak was traced to a tanker shipment of contaminated liquid ice cream.

An outbreak of *Salmonella typhimurium* in Illinois in 1985 affected over 170,000 people as a result of contaminated milk. What made this outbreak particularly disturbing was the fact that the strain of *S. typhimurium* involved demonstrated resistance to nine different antibiotics.

There are other known pathogens of greatest concern. For instance, the associated illness for pathogen *Salmonella typhi* is acute fever, diarrhea and potential intestinal rupture. The associated illness for pathogen *Shigella dysenteriae* is dysentery, with a fatality rate of up to about 20%. The associated illness pathogen *Escherichia coli* (*E. coli*) (O157:H7) is acute hemorrhagic diarrhea and possible long-term problems. The associated illness pathogen for *Vibrio cholerae* is severe diarrhea, with up to about 50% fatality rate.

A variety of strategies have been reported for the targeted delivery of antimicrobial agents to bacteria. In creating antibiotics for such pathogens, compounds were selected based on their ability to preferentially affect systems or features that are unique to microbe(s). They have also been selected based on being sufficiently different from analogous systems or features in host cells. However, many compounds that show very potent antimicrobial activity tend not to be suitable for use as therapeutics due to undesirable side effects or poor selective toxicity. Targeted delivery is expected to allow the use of alternative antimicrobial agents, such as nitric oxide (NO), that are less specific in the types of cells they affect and may even have broader impact. Yet, if delivered nonspecifically, undesirable side-effects may result. Furthermore, while a diverse range of strategies for targeted delivery of therapeutics have been explored for the selective delivery of chemotherapeutics to cancerous cells, they have only recently been investigated for the treatment of infectious disease.

For example, constructs based on chlorine$_6$ conjugated to polylysines of varied lengths and varied degrees of substitution have been investigated against representative gram-negative and gram-positive bacteria for the intracellular delivery of the photosensitizer (chlorine$_6$). In these studies, cells were treated with the conjugate and then exposed to 660 nm light, which triggers the generation of singlet oxygen and free radicals leading to cell death. While useful in localized applications, polylysine conjugates are generally not well suited for systemic administration. They tend to provide limited specificity in their delivery of attached drug moieties by entering host cells, as well as invading microbes.

Similar polylysine peptides have been used for the transduction of proteins across the membranes of mammalian cells.

Even liposomes have been explored for the intracellular delivery of aminoglycoside antibiotics. It has been reported that the liposome-encapsulated aminoglycosides demonstrated significantly improved potency over the corresponding free drugs, when evaluated against *Pseudomonas aeruginosa* for the treatment of pulmonary infections.

Additionally, filamentous phage has been used for the targeted delivery of chloramphenicol as a model antibiotic. These phage-based constructs incorporate a filamentous phage that had been selected from a phage library for specific binding to *S. aureus*. As anticipated, chloramphenicol-phage conjugates with 2,000-4,000 drug molecules/phage retarded *S. aureus* growth, while comparable concentrations of free chloramphenicol had no significant impact on growth. As with antibodies, the specificity of phage-derived peptides makes them very specific for the target pathogen. However, at the same time, their specificity may also prevent their utility with organisms other than the one for which they were designed.

Thus, there is an urgent need to develop new antibiotics and approaches for treating infections.

BRIEF DESCRIPTION OF THE DRAWINGS

FIG. 2 shows an example of a flow diagram of creating a CAMP conjugate with levofloxacin.

FIG. 11 shows chloramphenicol and the chloramphenicol-linker adduct.

FIG. 16 shows a survival curve illustrating the percent of survival rate of *E. coli* against a levofloxacin-peptide conjugate and a mortality curve illustrating the death percentage of *E. coli* against the levofloxacin conjugate. These curves were generated using the same data set and represent two approaches to presenting the data.

FIG. 21 shows hemolytic activity of (A) Pep-1, Pep-2, Pep-3, and Pep-4 and (B) acetylated Pep-1, Pep-2, Pep-3, and Pep-4.

DETAILED DESCRIPTION OF THE INVENTION

Figure 1:
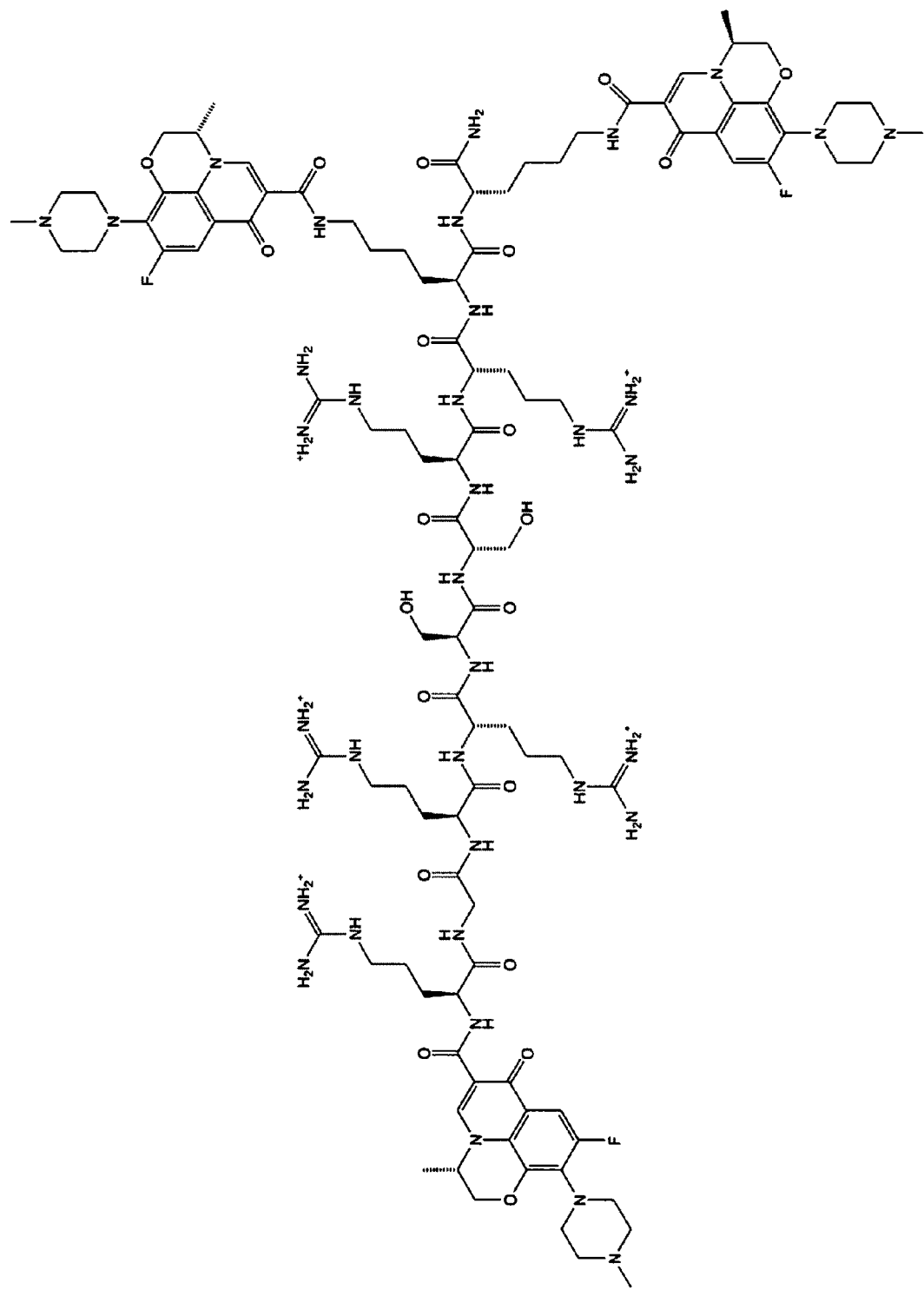
FIG. 1 shows an example of a levofloxacin-Peptide-4 conjugate.

The present invention relates to developing novel strategies for leveraging the therapeutic potential of cationic antimicrobial peptides (CAMPs), such as targeted delivery of antimicrobials.

Historically, antibiotics have been chosen based on their selective toxicity. However, many compounds with potent antimicrobial activity are not suitable for use as therapeutics due to undesirable side effects or poor selective toxicity. As a way around this problem, targeted delivery may allow the use of normally unsuitable antimicrobial agents by reducing their adverse side effects. Although a diverse range of strategies for the targeted delivery of therapeutics has been explored for the selective delivery of chemotherapeutics to cancerous cells, they have only recently been investigated for the treatment of infectious diseases.

Many of the properties that make antimicrobial peptides an effective defensive mechanism in higher organisms can also make them ideally suited as a platform for targeting microbes for delivery of potent antimicrobial compounds (such as NO, etc.). This platform may provide an invaluable therapeutic tool for treating infections (such as those in the gastrointestinal tract, respiratory system, circulatory system, lymphatic system, urinary system, muscular system, skeletal system, nervous system, reproductive system, etc.), and could allow the use of novel antimicrobial agents, which would otherwise be unsuitable as therapeutics.

Some interior surfaces of the body, such as the respiratory and the gastrointestinal (GI) tracts, are topographically equivalent to exterior surfaces of the body. Because these surfaces are constantly exposed to potentially pathogenic microbes and are conducive to bacterial growth, novel therapeutic agents and strategies are needed for treating infections of the respiratory and GI tracts, particularly those caused by antibiotic resistant pathogenic microbes. Select agents (such as *Francisella tularensis, Bacillus anthracis*, and *Yersinia pestis*, which are known to cause life-threatening pneumonic infections and may be rendered antibiotic resistant) are of particular concern as potential biological weapons.

Similarly, foodborne and waterborne pathogens (such as *Shigella dysenteriae, Vibrio cholera*, and *Salmonella typhi*) are considered potential biological threats that could be employed by terrorists to contaminate food and/or water supplies. While infections by many of these microbes are usually responsive to treatment with antibiotics, illness resulting from intentional exposure will likely involve organisms that have been engineered to be resistant to conventional antibiotics.

As a solution, CAMPs may be used. CAMPs provide an ideal model for the design of delivery vehicles that target many bacteria, both Gram-positive and Gram-negative. While there is debate regarding the specific antimicrobial mechanisms employed by CAMPs and the extent to which internal targets are involved, these peptides have been shown to attack and disrupt bacterial membranes. In targeting bacteria, CAMPs capitalize on a fundamental physical property of bacterial membranes (negative charge density). The present invention differs from known efforts in developing CAMP-based therapeutics in that the present invention aims to capitalize on their selective targeting, but does not rely on the peptide alone to kill the microbe. Instead, this strategy uses the peptide as a vehicle for the targeted delivery of more potent antimicrobial agents. Should the promise of targeted delivery of potent antimicrobial agents be realized, peptide-based drug conjugates (sometimes referred to as peptide-drug conjugates or peptide-antimicrobial agent conjugates) could provide powerful therapeutics for the treatment of a broad spectrum of infections, especially respiratory infections.

As an embodiment, smaller peptides are preferable to larger and more complex CAMPs because they are more easily synthesized and characterized. They also allow greater control in preparing drug-peptide conjugates. For example, a series of short peptides (12 to 10 residues) based on the C-terminal region of human beta-defensin-3 may be prepared since peptides based on this region had previously been reported to be potent against *E. coli*. Four decapeptides and their acetylated derivatives may be generated to evaluate how attachment of drug moieties through acylation to primary amino groups in the peptides and the associated loss in positive charge may affect their ability to target bacteria (such as *E. coli*) while leaving host cells (such as erythrocytes) unharmed. The performance of the free and acetylated peptides suggests a complex relationship between peptide charge and potency. Additional carrier peptides may be designed using different peptides, such as defensins (alpha and beta), cathelicidins, protegrins, indolicidins, histatins, tachyplesins, etc.

Model drug-peptide conjugates may be produced using, for example, levofloxacin and the decapeptide that showed the greatest potency when acylated. Using matrix-assisted laser desorption/ionization—time of flight (MALDI-TOF) mass spectrometry, one can analyze the loading of levofloxacin on the peptide. One can then evaluate the performance of the drug-peptide conjugates against *E. coli*. These studies can be expanded to include additional microbes (such as *F. tularensis* and *S. aureus*) and eukaryotic cells (such as epithelial cells and hepatocytes). Alternative linkage chemistries, peptide carriers and antibiotics may also be determined using these processes.

Unlike prior approaches that have been suggested for targeted delivery of antibiotics, this delivery strategy is not a pathogen-specific approach. Rather, it a broad antibacterial approach. For example, the present invention enables inhalation treatment of respiratory infections, oral treatment of gastrointestinal infections, etc. The modular nature of the proposed carrier peptides and the resulting drug-peptide conjugates makes creates a highly flexible and broadly applicable platform for treating such infections, including those in which microbes are resistant to conventional therapies. The ability to target delivery to the microbes dramatically expands the repertoire of potential antibiotic moieties to include compounds that are otherwise too cytotoxic for use.

Referring to the figures, FIG. 1 shows an example of a CAMP conjugate (i.e., levofloxacin-Peptide-4 as shown), and FIG. 2 shows an exemplified flow diagram of producing a CAMP conjugate. Steps include: identifying a suitable carrier peptide S205; identifying a suitable antimicrobial agent S210; creating a conjugate by conjugating the peptide with the antimicrobial agent S215; and evaluating and refining the conjugate S220. As one embodiment, the peptide is a short-peptide based on the sequence or portion of a sequence of a CAMP. As another embodiment, the peptide is directly connected to the antimicrobial agent or through the use of a linker segment. The antimicrobial agent may be connected to the peptide or the linker segment through either a stable or a cleavable bond. As another embodiment, the peptide carries and facilitates the delivery of the conjugated antimicrobial agent to a microbe.

In essence, The CAMP conjugate comprises at least one peptide conjugated with an antimicrobial agent. The peptide is a short peptide based on the sequence or portion of a sequence of a CAMP. Furthermore, the peptide is directly connected to the antimicrobial agent or through a linker segment. The antimicrobial agent being connected to the peptide or the linker segment through stable or cleavable bonding. Moreover, the peptide carries and facilitates the delivery of the conjugated antimicrobial agent to a microbe.

In yet another embodiment, the linker segment affixes the antimicrobial agent to the peptide through acylation of the amino group of the N-terminus of the peptide. As a further embodiment, the peptide carries and facilitates the delivery of the conjugated antimicrobial agent to a microbe.

In yet a further embodiment, the antimicrobial agent is directly attached to the peptide.

The peptide may be a short peptide. "Short peptide" refers to any peptide that has about 4 residues to about 100 residues. As an embodiment, the peptide may have about 4 residues to about 10 residues. In addition, it is possible that the peptide may have less than 4 residues, such as non-natural amino acids. Examples of non-natural amino acids include, but are not limited to, oranthene (which is lysine minus one amino acid), N—N-dimethyl substituted lysine residue, fluoroaniline, etc.

In yet a further embodiment, the CAMP is a beta-defensin (also hereinafter denoted as β-defensin). β-defensin based peptides may include any peptide having at least a portion of an amino acid sequence of a human β-defensin, such as human β-defensin-3. For instance, such portion includes peptides based on the last 10 residues of the amino acid sequence comprising RGRKCCRRKK (SEQ ID NO. 4). While this example uses the tail end of the amino acid sequence, the sequence can be any portion of an animal peptide. For instance, the sequence or portion of the sequence may be in the front, middle, or end of the peptide sequence. Furthermore, any number of residues may be considered from the sequence or portion of the sequence.

Any residue of any amino acid sequence may be modified to create particular variants. As an embodiment, using the above last 10 residues as an example, the partial amino acid sequence may be RGRKSSRRKK (SEQ ID NO. 2) (where the fifth and sixth amino acid are replaced with serine). As another embodiment, the partial amino acid sequence may be RGRRSSRRKK (SEQ ID NO. 3) (where the fourth amino acid of the above last 10 residues are replaced with arginine, and where the fifth and sixth amino acid of the above last 10 residues are replaced with serine). As another embodiment, the partial amino acid sequence may be RGRKSSRRKK (SEQ ID NO. 2) and an amide group located on the C-terminus (SEQ ID NO. 5). As another embodiment, the partial amino acid sequence may be RGRRSSRRKK (SEQ ID NO. 3) and an amide group located on the C-terminus (SEQ ID NO. 6).

Using small synthetic peptides allows the incorporation of non-natural amino acids, Such incorporation may introduce new functional groups (such as aldehydes) into the peptide that allow linkage chemistries that are not accessible in natural peptides and proteins.

In the broader sense, conjugation chemistry is tailored to the functional groups present on the drug (e.g., antimicrobial agent) and the linkage chemistry that they allow. If necessary, a bridge (e.g., succinic or glutaric acid) can be incorporated that provides groups compatible with linking the drug to the peptide. In such a case, a group (e.g., a carboxylic acid) on the bridge is used to form a linkage with the drug, and another functional group (e.g., a second carboxylic acid) on the bridge is used to form a linkage with reactive functional groups (e.g., primary amines) present in the peptide.

The antimicrobial agent can be a host of various compounds. Nonlimiting examples include levofloxacin, chloramphenicol, diazeniumdiolates, etc.

The connection between the peptide and antimicrobial agent can be made using the side chain groups present in the peptides and/or the amine or carboxyl groups at the ends of the peptides. The antimicrobial agent can be attached directly to these groups, or through a bridging group (e.g., succinic or glutaric acid). In either approach, the nature of the bond connecting the drug molecule to the peptide or linking group can either be stable to environmental and biological processes or subject to cleavage by the same processes. Examples of stable bonds include, but are not limited to, secondary amines formed via reductive amination, triazine-based linking groups, etc. Examples of cleavable bonds, include but are not limited to, ester bonds, amide bonds, etc. Depending on the nature of the connected groups, cleavable bonding can be susceptible to cleavage by environmental and/or biological processes. For example, an ester bond connecting a drug moiety to the side chain of a serine residue in the peptide may be recognized by enzymes (such as lipases) that hydrolyze such bonds. Furthermore, ester linkages can be prone to hydrolysis under alkaline conditions. The susceptibility of these and other cleavable bonds to these processes is dependent on the nature of the bond and the groups connected by it.

For those CAMP conjugates using a stable linkage, the attached drug would still be effective when attached to the carrier peptide. As for those CAMP conjugates using a cleavable linkage, the drug (i.e., antimicrobial agent) tends to be released slowly through environmental processes or through biological processes, such as through enzymes associated with the targeted microbes (e.g., bacterial lipases).

Figure 3:
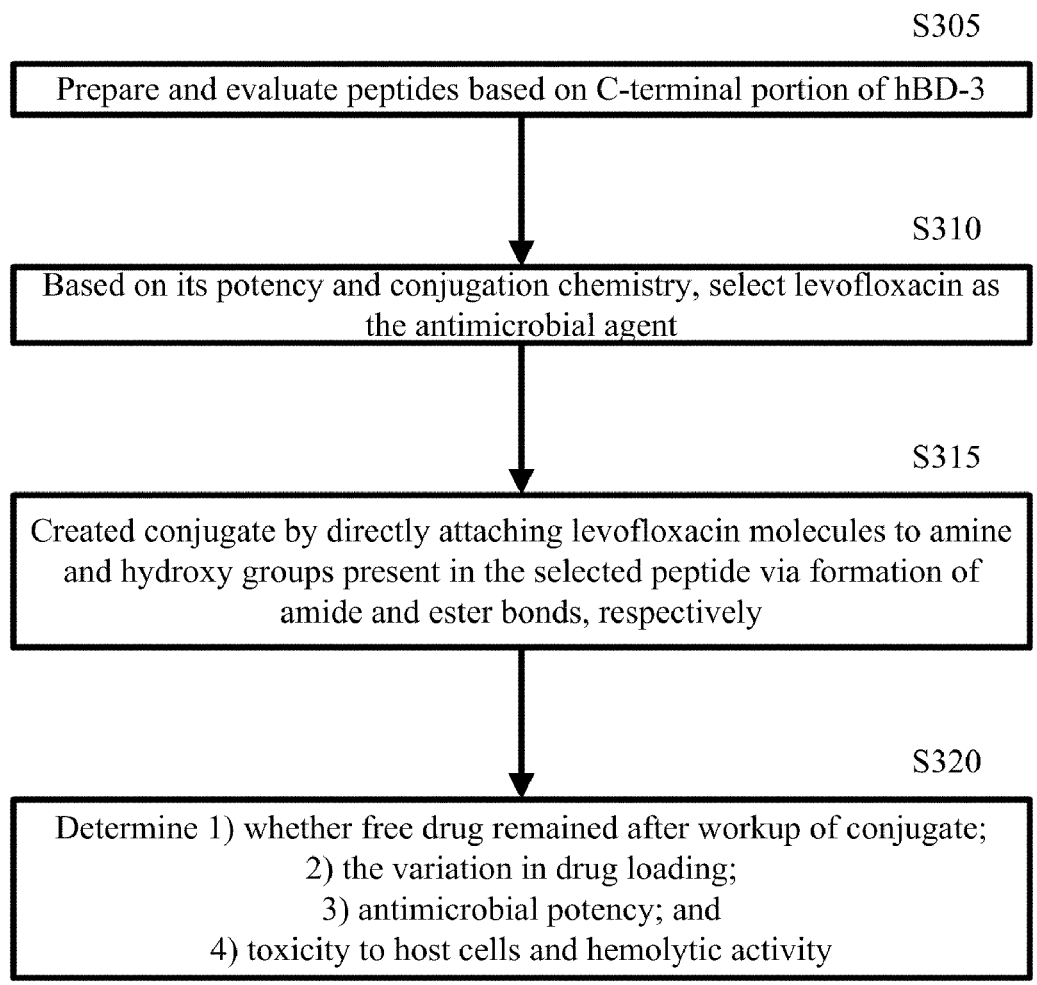
FIG. 3 shows a specific example of a flow diagram of creating a levofloxacin-hBD-3 conjugate.

To illustrate a specific example of developing a antimicrobial agent-peptide conjugate, reference is made to FIG. 3. In this model, peptides need to be first prepared and evaluated S305. The peptides may be based on C-terminal portion of hBD-3. Then, an antimicrobial agent needs to be selected S310. Here, levofloxacin is selected as the model example because of its potency and conjugation chemistry. However, it should be noted that the present invention used levofloxacin only as an example and thus is not limited to only this drug. Next, the conjugate may be created by directly attaching levofloxacin molecules to amine and hydroxy groups present in the selected peptide via formation of amide and ester bonds, respectively S315. Afterwards, what needs to be determined are 1) whether free drug remained after workup of conjugate; 2) the variation in drug loading; 3) antimicrobial potency; and 4) toxicity to host cells and hemolytic activity S320. If the results of these determinations are satisfactory, then the created antimicrobial agent-peptide conjugate (like the model levofloxacin-hBD-3 conjugate) is deemed successful.

I. Peptides and Compounds

A. CAMPs

Cationic antimicrobial peptides (CAMPs) are essential elements of innate immunity in higher organisms that contribute to the first line of defense against infection. While CAMPs exhibit a diverse range of amino acid sequences and structural properties, they are typically small amphipathic peptides that are rich in lysine and arginine residues. In addition, they exert a direct antimicrobial affect on a broad-spectrum of microbes, such as Gram-positive and Gram-negative bacteria, fungi and viruses.

Small antimicrobial peptides can be loosely classified into four groups based on common structural themes: (1) linear α-helical peptides, (2) linear extended peptides (with sequences dominated by one or more amino acids), (3) peptides containing loop structures, and (4) peptides with more defined structures constrained by intramolecular disulfide bonds.

Vertebrate defensins are small CAMPs that contain one or more intramolecular disulfide bonds and can be grouped into defensin sub-families based on functional and structural properties.

The antimicrobial mechanisms employed by most CAMPs are believed to involve disruption of the bacterial membrane. In these models, the cationic peptides initially associate with the outer surface of bacterial membranes, which tend to contain a greater abundance of lipids with negatively charged head groups than do eukaryotic membranes. Moreover, the presence of cholesterol in eukaryotic membranes can make them more resistant to disruption by CAMPs. While multiple membrane disruption schemes have been proposed, these mechanisms appear to be peptide dependent. Generally, proposed membrane disruption mechanisms range from a "barrel-stave" model to a "carpet model". The "barrel-stave" model describes a model where amphipathic helical peptides insert into the membrane to form helical bundle structures that contain large central pores. The "carpet model" describes a model where peptides gather and concentrate at the membrane surface, interact with the anionic lipid head groups, and cause distortions in the lipid bilayer and the formation of peptide-lined openings in the membrane.

B. Defensins

Defensins are a family of potent antimicrobial peptides produced by various types of cells in the body, including but not limited to neutrophils, macrophages, epithelial cells and leukocytes. These small antimicrobial peptides are a major component of the first line of defense against invading pathogens. They are known to demonstrate broad antimicrobial activity against bacteria, fungi, parasites and viruses. Like other CAMPs, defensins are believed to function as least in part by binding to microbial membranes and increasing membrane permeability of those microbes.

In mammals, there are three main families of defensins, namely α-defensins, β-defensins and θ-defensins, that share some common features. They are generally rich in basic amino acid residues, such as arginine and lysine. In α-defensins and β-defensins, six cysteine residues form three intramolecular disulfide bonds, stabilizing the 3D structure that contains a triple-stranded antiparallel β-sheet. α-defensins are produced primarily in neutrophils and small intestinal paneth cells. β-defensins are produced in leukocytes and epithelial cells. The majority of work to date has focused on four distinct human β-defensins, namely human β-defensin-β ("hBD-1"), human β-defensin-2 ("hBD-2"), human β-defensin-3 ("hBD-3") and human β-defensin-4 ("hBD-4"). θ-defensins are short peptides, which are produced by rhesus macaques. Unlike other defensins, θ-defensins are unique in that they are cyclic peptides, where the N- and C-termini have been linked through a backbone peptide bond. Humans appear to possess a defective gene for θ-defensins, and they do not produce these peptides.

C. Beta-Defensins

Despite demonstrating limited sequence similarity, beta-defensins (a subclass of defensins expressed in mammals and birds) are characterized by a shared three-dimensional folded conformation that combines an N-terminal α-helical segment and a small three-stranded antiparallel β-sheet. In beta-defensins, the folded structure may be stabilized by a conserved network of three intramolecular disulfide bonds. Beta-defensins are predominantly expressed by epithelial cells. However, low-level expression of beta-defensins has been observed in other tissues, such as the heart and the thymus. Of the known human beta-defensins (hBDs), human beta-defensin-1 is constitutively expressed, while the expression of other hBDs appears to be primarily induced by the presence of pathogens and pathogen associated compounds. To date, the majority of research has focused on hBD-1, hBD-2, hBD-3, and hBD-4. But analyses of human genomic sequences have revealed the existence of five beta-defensin gene clusters containing approximately 30 known and potential beta-defensin genes. These peptides demonstrate antimicrobial effectiveness against a broad spectrum of Gram-positive and Gram-negative bacteria, fungi, and some enveloped viruses, with hBD-3 demonstrating broader antimicrobial effectiveness than the other three human beta-defensins. Additionally, the antimicrobial potencies of hBD-1, hBD-2, and hBD-4 are negatively impacted by the ionic strength of the medium, while hBD-3 retains its antimicrobial activity even at elevated salt concentrations. While beta-defensins are capable of directly exerting antimicrobial activity against invading pathogens, they also demonstrate chemotactic properties, thus bridging innate immunity and adaptive immunity.

Figure 4:
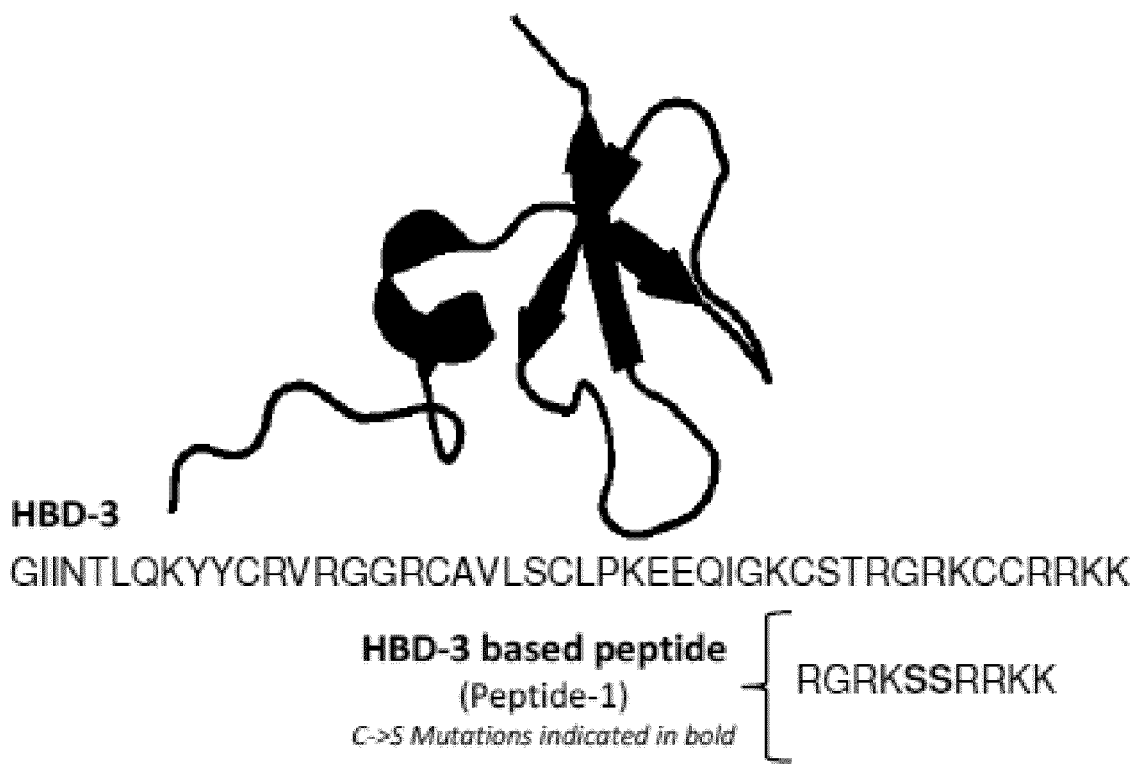
FIG. 4 shows an illustration of the three-dimensional structure and amino acid sequence of hBD-3.
Figure 5:
FIG. 5 shows another version of the amino acid sequence of hBD-3.

Recently, short peptides with sequences based on portions of the amino acid sequence of hBD-3 have been reported to exhibit varied antimicrobial potencies against *E. coli* and *S. aureus*. FIG. 4 and FIG. 5 illustrate the amino acid sequence of hBD-3. Regions residing in a defined secondary structure in the folded peptide are labeled "α" for "-helix" configuration and "β" for a "-strand" configuration. Residues corresponding to the antimicrobially active decapeptide are denoted with the expression "RGRKCCRRKK" (SEQ IQ NO. 4).

In these truncated peptides, serine residues may be substituted for cysteine residues present in the full-length peptide to eliminate the potential of the formation of disulfide bonds. The shortest peptide that demonstrated significant antimicrobial potency is a decapeptide with a sequence based on the C-terminal portion of hBD-3, namely Arg36-Lys45. In a broader context, this decapeptide represents one of the shorter peptides that demonstrate significant antimicrobial activity. Moreover, it cannot be readily grouped with any of the structural classes as noted above. In the folded full-length peptide, the segment corresponding to -Lys-Ser-Ser-Arg-provides the interior beta strand of the antiparallel beta sheet. Outside of the context of the full-length peptide, it is unlikely that the corresponding residues in the decapeptide are in a similar conformation as they are in the parent peptide. Furthermore, the distribution of hydrophobic and hydrophilic residues within the peptide sequence is not consistent with the pattern that is normally associated with the formation of an amphipathic helix.

The fact that the decapeptide described above retains antimicrobial activity in the absence of the remainder of hBD-3 makes it an appealing model for exploring the relationship between net charge, charge distribution, and antimicrobial activity. To study these effects, a series of peptides have been designed based on the decapeptide in order to evaluate how these properties contribute to their antimicrobial potency.

D. Nitric Oxide

Work conducted over the past two decades has established NO as a major signaling molecule with diverse physiological functions, including neurotransmission, vasodilation, immune regulation and host defense against pathogenic microorganisms. While the immunoregulatory functions of NO are well documented, less is known about its antimicrobial function. Production of NO is associated with macrophage response to infection. Being a reactive nitrogen species, NO demonstrates broad-spectrum antimicrobial activity and is believed to exert its antimicrobial activity by inflicting nitration damage and indirectly causes oxidative damage to many microbial systems. It is generally believed that bacterial DNA and the DNA repair machinery are targets of NO related damage. A variety of other proteins are also damaged in the process by nitration and oxidative damage.

The remarkable variety of bioregulatory roles that have been identified for the nitric oxide radical has produced a need for compounds that can conveniently generate NO both for use in laboratory studies and as potential drugs targeting delivery of NO to specific biological sites. Among several classes of NO donor compounds which have been developed, diazeniumdiolates ("NONOates"), ions of structure $R^1R^2N$ [N(O)NO]$^-$, have proven to be one of the most versatile and widely used. Diazeniumdiolate compounds provide an excellent source for the controlled release of NO, both in vitro and in vivo. When dissolved in buffers or cell culture media, they undergo spontaneous acid catalyzed dissociations with well behaved first-order processes to release the parent amine and quantifiable amounts of NO.

since their NO release rates have half-lives ranging from ~2 seconds to ~20 hours, depending on the structure of the parent amine and substituents on the $O^2$ position, they have proven to be a particularly versatile class of NO providers. Their versatility can be extended through $O^2$-derivization of the —[N(O)NO]$^-$ group to form diazeniumdiolate conjugates that do not release significant amounts of NO until the terminal substituent is removed by enzymes or other biological processes at targeted sites. Diazeniumdiolates have found application as NO releasers in biomedical research studies exploring NO's vasodilatory, antiplatelet, and cytostatic properties.

Figure 6:
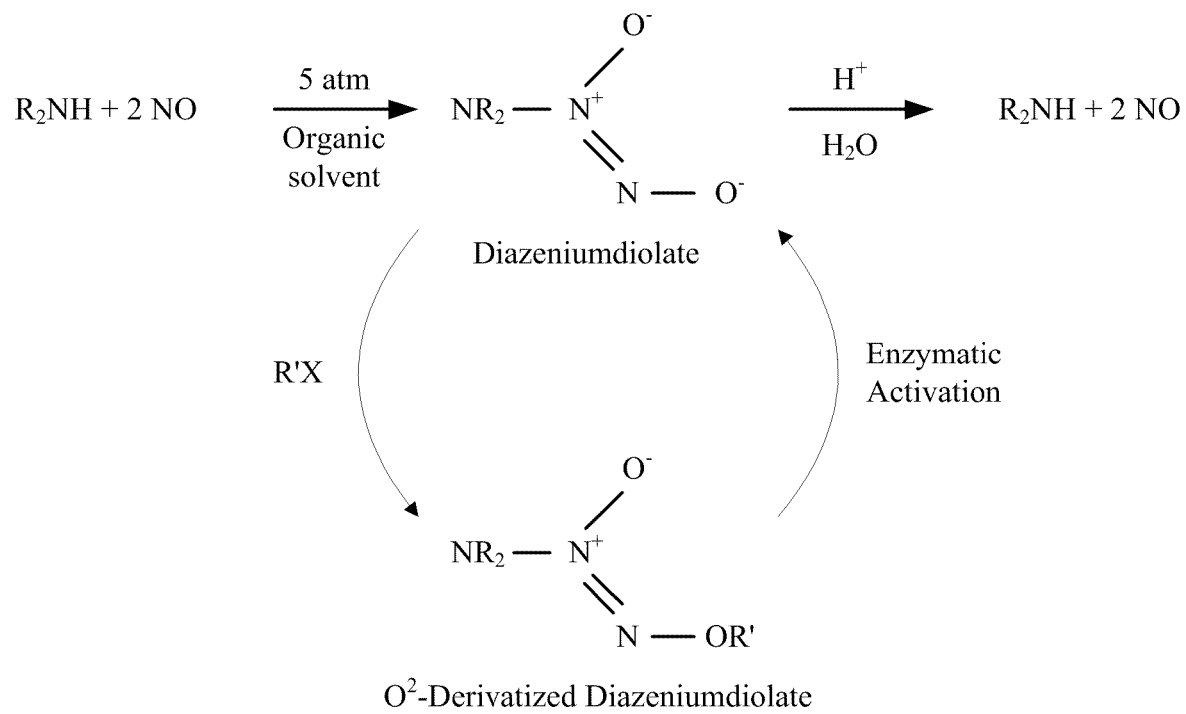
FIG. 6 shows an example of synthesizing diazeniumdiolates.

As shown in FIG. 6, diazeniumdiolates are readily synthesized by reaction of a secondary amine with NO gas at 5 atm pressure to produce solids that are stable at 0° C.

The multiple roles NO plays in cell signaling and host defense have lead to considerable interest in potential therapeutic applications of NO and NO-releasing derivatives, such as diazeniumdiolates. The antimicrobial activity of NO led to the incorporation of silicon aminoalkoxides in the synthesis of sol-gels. The porous silica that was formed contained amine functionalities, which were in turn used to generate diazeniumdiolates. It was hypothesized that thin films of such materials would release NO under physiological conditions, which would serve to prevent the formation of biofilms on the sol-gel surface. Such biofilms can be persistent problems associated with catheters, artificial joints and other implants; often, they threaten the health of patients. Ultimately, it was determined that the nature of the silicon aminoalkanoate used in forming the sol-gel influenced the rate of NO release and stability of the diazeniumdiolate. They also found that these materials were more resistant to biofilm formation than were comparable materials that did not contain diazeniumdiolates, illustrating the potent antimicrobial properties of this class of compounds.

Two groups have reported distinct strategies for conjugating diazeniumdiolates to peptides or proteins. One set out to develop a general strategy for attaching diazeniumdiolate groups to peptides and proteins in order to take advantage of the unique functions of the proteins to direct delivery of the attached diazeniumdiolate. In this approach, a methoxymethyl-protected monodiazeniumdiolate of piperiazine was conjugated to both human and bovine serum albumin utilizing an asymmetric linker, maleimidobutyric acid. The diazeniumdiolate derivative was attached to the protein by forming an amide bond between the carboxyl group of the linker and the side chains of lysine residues in the protein under conditions that allowed the protein remain folded. Another strategy was engineering a diazeniumdiolate-peptide conjugate in order to target the prostate and metastatic prostate cancer. Diazeniumdiolates were conjugated to the C-terminus of the peptide via and acetoxymethoxy linkage at the $O^2$ position of the diazeniumdiolate. By using a peptide with an amino acid sequence recognized by a prostate specific antigen (PSA) with proteolytic activity, breakdown of the diazeniumdiolate and release of NO is initiated by hydrolysis of the C-terminal ester by PSA.

II. Antibiotic-CAMP Conjugates

Figure 7:
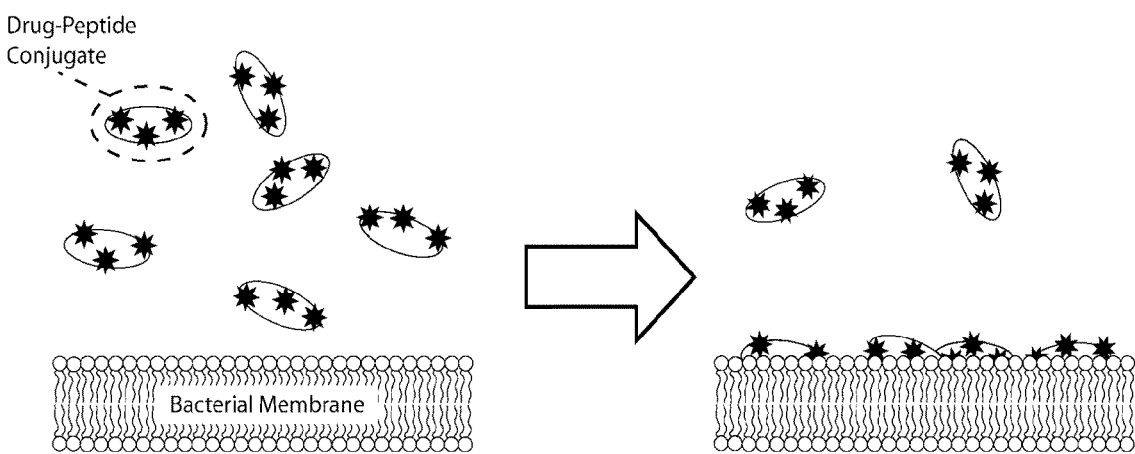
FIG. 7 shows an example of drug-peptide conjugates being attracted to bacterial membranes.

Generally, constructs based on short antimicrobial peptides may be engineered for the targeted delivery of antibiotics and cytotoxic agents. As illustrated in FIG. 7, this process can be achieved by capitalizing on the ability of such peptides to specifically target microbes largely due to electrostatic interactions between the cationic peptides and the anionic surface of the bacterial membrane. Because these peptides generally target a fundamental physical property of bacterial membranes, conjugates based on CAMPs should be effective against a broad spectrum of microbes, while leaving host cells unharmed.

The term "conjugate" refers to CAMPs with covalently attached antibiotics and antibiotic-linker adducts (e.g., antibiotic-CAMP conjugate).

The term "adduct" refers to an antibiotic with a covalently attached linker segment (e.g., drug-linker adduct).

The main function of the peptide is not to directly kill the microbe, albeit destroying the microbe may be a beneficial side-effect. Instead, the main function is to have the peptide serve as a carrier and facilitator for the delivery of one or more attached antimicrobial agents. Ideally, the antibiotic delivered by the conjugate would inflict antimicrobial activity against targeted bacteria at concentrations significantly lower than that required for the carrier peptide itself to kill them.

Figure 8:
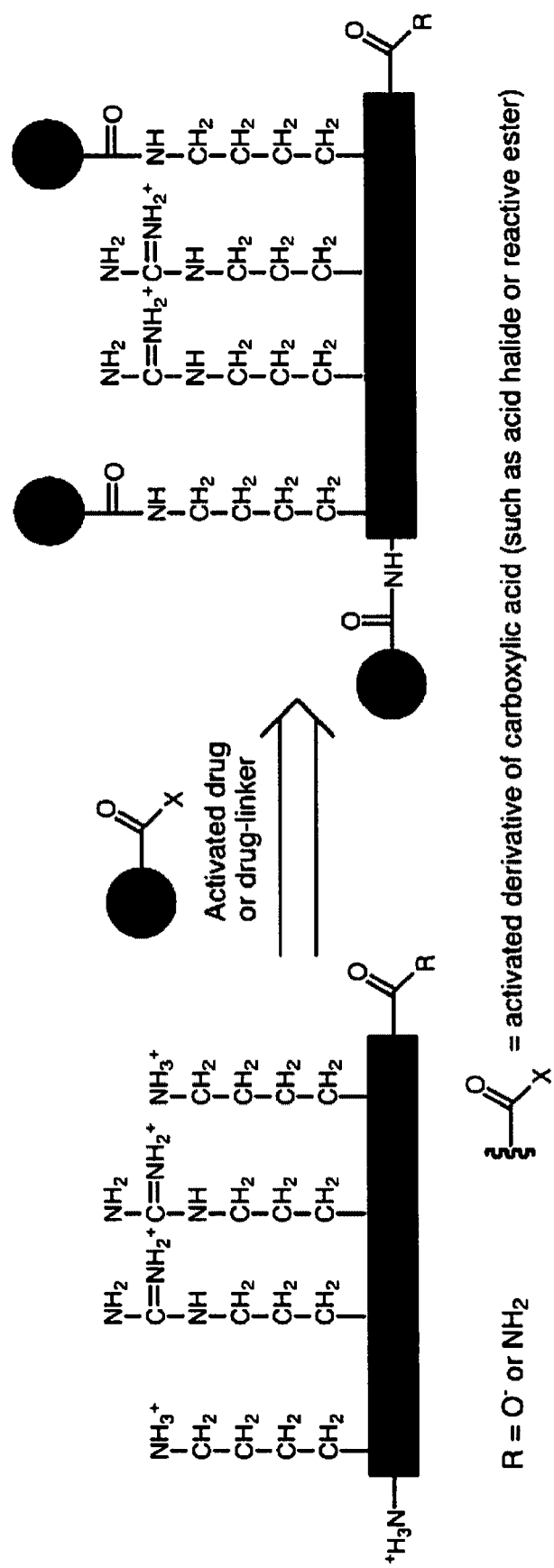
FIG. 8 shows a general strategy of conjugating antibiotics to a peptide carrier via carboxylic acid groups present in the drug molecule.

As one embodiment, referring to FIG. 8, drug moieties or drug-linker adducts bearing carboxylic acid groups may be attached to a peptide carrier via amide bonds formed with the primary amino groups of the N-terminus and lysine side chains in the peptide. This figure illustrates a scheme for conjugating antibiotics attached (dark circles) to the peptide carrier. The strategy involves activating a carboxylic acid group on the drug molecule or the linker to form amide bonds with free amino groups present in the peptide. The performance of free peptides and acetylated peptide derivatives can be evaluated using in vitro antimicrobial, hemolytic and cytotoxicity assays to identify potential peptide carriers and hone their targeting ability.

To initially evaluate the ability of peptides and their respective derivatives to effectively target bacteria, antimicrobial potency of *E. coli* may be used. Similarly, hemolytic and cytotoxicity assays may provide a means of evaluating whether the peptides and their derivatives are likely to attack host cells.

Designing peptide carriers for maximum performance of fully-loaded drug-peptide conjugates where all available sites of attachment are occupied is essential for consistent performance. By focusing on fully-loaded conjugates, a homogeneous product may be created without having to resort to complex and likely inefficient strategies for resolving various antibiotic-CAMP species that may be formed otherwise.

In other instances, a heterogeneous product may be produced. For instance, the levofloxacin conjugates that have been prepared are heterogeneous and comprise three different species that differ in the degree of loading. For example, loading may occur in all of the Lys residues and the N-terminus. As another example, loading may occur along the side chain —OH groups of serine residues.

Each lysine residue represents a site for attachment of drug groups. A result of attachment is a net loss in positive charge in the conjugated peptide, which may impact the targeting capacity of the delivery vehicle. Therefore, variations in sequence focus primarily on the number and position of lysine and arginine residues.

Not only does such focusing help refine the balance between charge and loading in antibiotic-CAMP conjugates, but also helps enhance antimicrobial potency coupled, while minimizing hemolytic activity.

It should be noted that serine residues can be incorporated within the peptide sequence to introduce hydroxyl groups. These hydroxyl groups can in turn be used to attach drug molecules through the formation of ester bonds. Such bonds may be more amenable to enzymatic cleavage than the side chain amide bonds formed with Lys residues.

To employ CAMPs and create CAMP-antimicrobial agent conjugates, three major aspects need to be considered. First, suitable carrier peptides need to be identified. As an embodiment, small cationic peptides with sequences based on naturally occurring antimicrobial peptides can be engineered to evaluate the ability of free peptide(s) as well as the conjugated peptide to target bacteria preferentially over host cells. Sequences can be varied to probe how the net charge, charge distribution, degree of loading, nature of covalent attachment, and positioning of substitution may impact the performance of the peptide.

Second, suitable antimicrobial agents need to be identified and conjugated. As one embodiment, antibiotics may be used as the antimicrobial agent to be delivered by the peptide carriers. As another embodiment, diazeniumdiolates and NO may be used. Diazeniumdiolates are versatile NO sources. As a nonlimiting example, the performance of a methoxymethyl-protected monodiazeniumdiolate of piperazine may be evaluated. The present invention also allows for other and additional diazeniumdiolate variants that may be used to improve and refine performance of the free drug.

Third, conjugates should be evaluated and refined. As an embodiment, drug-peptide conjugates may be assembled. As another embodiment, diazeniumdiolate-peptide conjugates may be assembled. Their performances may be evaluated in antimicrobial hemolytic and cytotoxicity assays. This information may be used to direct the engineering of the next generation of peptides and drug/diazeniumdiolates and conjugates. The process may be repeated until a peptide-drug combination or a peptide-diazeniumdiolate combination is identified that embodies both superior antimicrobial potency, and minimal hemolytic activity and cytotoxicity.

As one embodiment, the present invention uses constructs derived from CAMPs, such as, but not limited to, human β-defensin-3, for the delivery of antimicrobial agents. This coupling capitalizes on the CAMPs' abilities to specifically target microbes, which are in large part often due to electrostatic interactions between the cationic peptides and the anionic surface of the bacterial membrane.

Referring again to FIG. 7, drug-peptide conjugates which are positively charged, may be attracted to bacterial membranes. The outer surface of bacterial membranes tend to be rich in lipids with negatively charged head groups. The electrostatic attraction allows for the attached antibiotic moieties to be delivered to the microbe.

While the issue regarding the specific mechanism employed by antimicrobial peptides remains debatable and whether secondary targets are involved, these peptides surprisingly attack bacterial membranes. Ultimately, such attack disrupts membrane integrity and kills the microbe. Therefore, an added, surprising benefit of using delivery constructs based on antimicrobial peptides is their ability to weaken or disrupt bacterial membrane integrity, which would facilitate entry of the associated antimicrobial agent. Moreover, the peptides may cross the bacterial membrane prior to disruption and may target groups within the microbe. In this scenario, the peptide would carry the attached antibiotic with them providing the ferried drug molecules access to the interior space of the targeted microbe.

The membranes of eukaryotic cells are generally more resistant to disruption than are bacterial membranes. Higher resistance generally provides an added mechanism for the targeted delivery of antimicrobial agents into the interior of invading microbes. By focusing on the bacterial membrane and not targeting specific surface proteins, conjugates based on antimicrobial peptides should be effective against a broad spectrum of microbes, while leaving host cells unharmed. In this strategic embodiment, the main function of the peptide is then not to directly kill the microbe. Rather, it is to serve as a carrier and facilitator for the delivery of an attached antimicrobial agent.

Ideally, the antibiotic-CAMP conjugate and the delivered antibiotic may exert antimicrobial effect at concentrations that are significantly lower than that required for the peptide along to kill the microbe(s).

A. Identification of Suitable Carrier Peptides

As an embodiment, the present invention may use small peptides. These small peptides may be based on, for instance, the amino acid sequence of the C-terminal region of the potent antimicrobial peptide hBD-3.

Short peptides (about 14- to about 10-residues) based on this region of hBD-3 have been reported to be potent against E. coli, with $EC_{90}$'s ranging from 1-10 µg/ml. These peptides generally provide an excellent template for engineering small antimicrobial peptides to serve as carriers. They contain multiple lysine and arginine residues. Additionally, they provide a high degree of control over the degree of loading and sites of attachment through the exchange of lysine and arginine residues in the sequence. The relatively small size of these peptides makes them more synthetically accessible than larger antimicrobial peptides. Furthermore, it tends to make them better suited to serve templates for future designs of peptide mimetics for improved robustness in vivo.

The initial peptide (Peptide-1 or Pep-1) and three sequence variants may be designed to evaluate how attachment of drug moieties through acylation and the associated loss in positive charge may affect activity and elucidate design criteria for minimizing impact.

The sequence of Peptide-1 may be denoted as (RGRKSS-RRKK) (SEQ NO. 2). This ten-residue peptide is based on the C-terminal region of hBD-3. In Peptide-1, serine residues may be used in place of cysteine residues present in the parent hBD-3. Reportedly, Peptide-1 is known to demonstrate antimicrobial potency at concentrations as low as 4 µg/ml. Fully acylated, this peptide may have a net charge of about +3 at pH of about 7 (as compared to +7 for the unmodified peptide).

The three sequence variants of Peptide-1 may be respectfully referred to as Peptide-2 (also Pep-2), Peptide-3 (also Pep-3), and Peptide-4 (also Pep-4).

Peptide-2 may have a sequence denoted as (RGRRSSR-RKK) (SEQ ID NO. 3). Here, Lys-4 of Peptide-1 has been replaced with an Arg residue. This replacement acts as a conservative substitution that can effectively eliminate a site that could be acetylated. Moreover, such generally helps retain the basic character of the position. Fully acylated, this peptide may have a net charge of about +4 at a pH of about 7 (as compared to +7 for the unmodified peptide).

Peptide-3 may have a sequence denoted as (RGRKSSR-RKK-NH2) (SEQ 10 NO. 5). Here, the C-terminal carboxyl group of Peptide-1 has been blocked by forming the C-terminal amide. This blockage eliminates the only acidic group in the peptide. Fully acylated, this peptide may have a net charge of about +4 at a pH of about 7 (as compared to +8 for the unmodified peptide).

Peptide-4 may have a sequence denoted as (RGRRSSR-RKK-NH2) (SEQ ID NO. 6). This peptide combines both the sequence modifications present in Peptide-2 and Peptide-3. Thus acylated Peptide-4 may have a +5 charge at a pH of about 7 (as compared to +8 for the unmodified peptide).

Peptides used may be custom synthesized by a number of companies (such as CelTek Bioscience, LLC of Nashville, Tenn. or Peptides International, Inc. of Louisville, Ky.) and/or by using various protocols. For example, fully acetylated derivatives of the peptides may be prepared by dissolving the unmodified peptides in 50 mM ammoniumbiocarbonate, followed by adding a methanolic solution of acetic anhydride. Using this protocol, which may be found the website of IonSource, LLC, the degree of acetylation for each peptide may be determined by MALDI-TOF mass spectrometry.

As another protocol example, these peptides may be manually synthesized using standardized solid-phase peptide synthesis ("SPPS") and 9-fluoroenylmethoxycarbonyl ("Fmoc") chemistry. Fmoc chemistry is an amine protection strategy that may be incorporated to prevent unwanted reactions at the α-amino group of the residue. In other words, the α-amino groups on amino acids may be provided temporary protection as they are being coupled. Another example of peptide synthesis includes SPPS based on t-butoxycarbonyl ("Boc") chemistry, which is another amine protection strategy.

Figure 9:
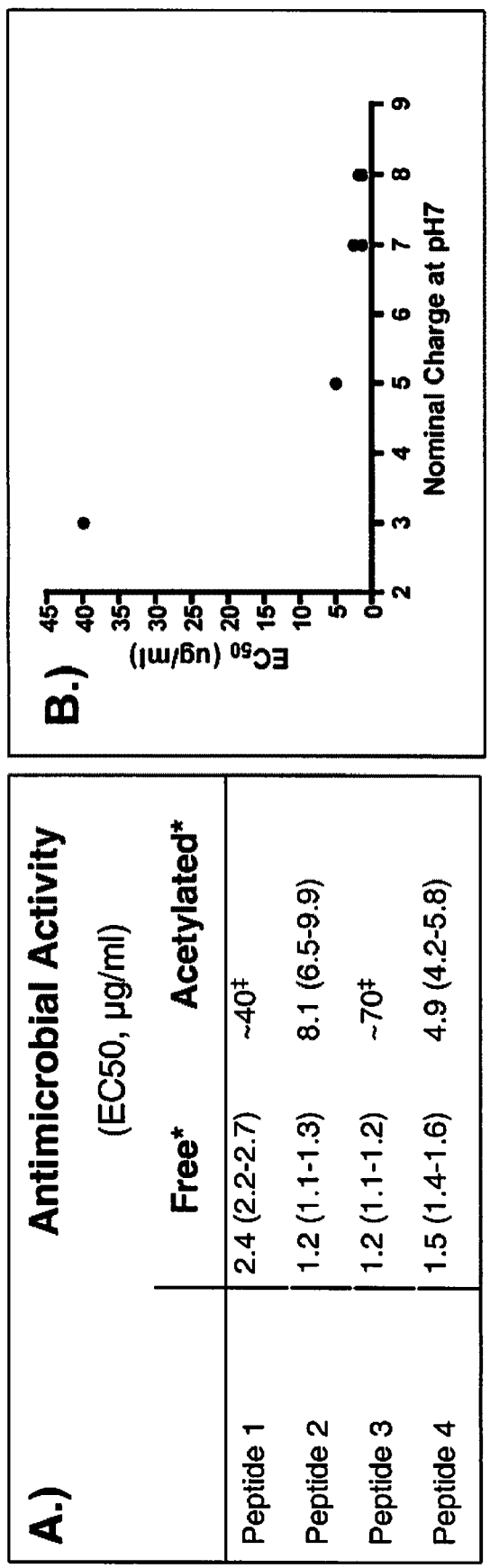
FIG. 9 shows an exemplified graph of antimicrobial activity ($EC_{50}$) for peptides and their acetylated derivatives, as well as an exemplified graph of the relationship between antimicrobial activity and nominal peptide charge at pH7.

The antimicrobial activities of the peptides and their acetylated derivatives may be assessed using K-12 E. coli and assays based on an existing protocol used to study derivatives of hBD-3. The bacteria may be grown to mid-log phase in Luria Bertani (LB) broth. Aliquots of the culture may then be diluted (to a cell density of about $10^6$ CFU/ml) into 10 mM sodium phosphate at a pH of about 7.5. Each of the aliquots may contain varied concentrations of peptide or acetylated peptide. The diluted bacterial cultures may then be incubated for about 2 hours at a temperature of about 37° C. After the proscribed time, serial dilutions of the assay cultures may be plated onto LB agar plates, and then allowed to incubate overnight at a temperature of about 37° C. After incubating, colonies may be counted. Dose-response curves may be prepared to calculate $EC_{50}$'s. Results of these experiments are shown in FIG. 9. Part A of this figure shows antimicrobial activity ($EC_{50}$) for peptides and their acetylated derivatives. Part B of this figure shows a graph illustrating relationship between antimicrobial activity and nominal peptide charge at pH7.

Part B also demonstrates that going from a formal charge of about +8 to about +5 results in only a slight decrease in potency. However, peptides with a charge of about +5 appear to be significantly more potent than those with a charge of about +3. To determine whether this trend relates to the correlation between the formal charge and performance of antibiotic-CAMP conjugates, it may be helpful in performing similar studies using antibiotic-CAMP conjugates.

Figure 10:
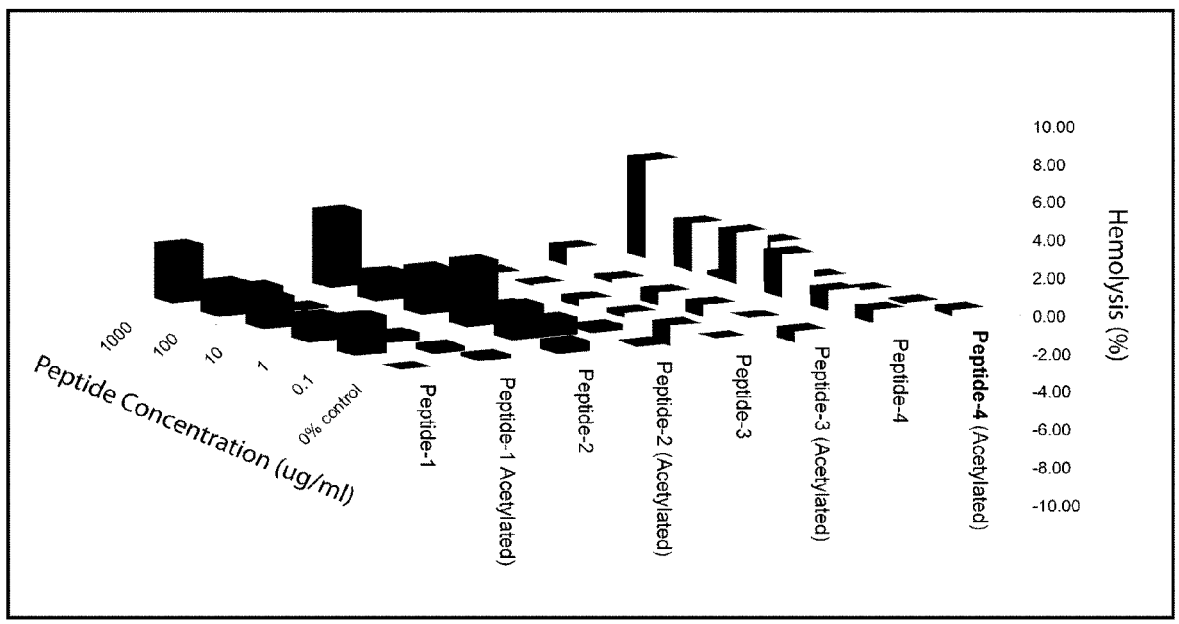
FIG. 10 shows an exemplified graph of hemolytic activity of Peptide-1, Peptide-2, Peptide-3, and Peptide-4 and their acetylated derivatives.

Hemolytic activity may be assayed by, for example, incubating horse erythrocytes (e.g., Hemasource Inc. of Eugene, Oreg.). Varied peptide concentrations in phosphate buffered saline (e.g., Cellgro, produced by Mediatech, Inc. of Manassas, Va.) may be used for the incubation process. Hemolysis may be quantified by pelleting cells after incubation using centrifugation, and then measuring the absorbance of the supernatant at about 540 nm. As shown in FIG. 10, hemolytic data suggests that Peptide-1, Peptide-2, and Peptide-4 may show some low-level hemolytic activity at very high concentrations. However, none of the acetylated peptides appear to demonstrate hemolytic activity (less than 1%).

While the results shown in FIG. 10, suggest that the acetylated peptides target bacteria and leave the erythrocytes unharmed, it may be necessary to similarly evaluate the hemolytic activity of the antibiotic-CAMP conjugates. The attached drugs may likely have significantly greater impact on the physical properties of the peptides than do acetylation. Here, performance in hemolytic and antimicrobial assays may be used to gauge specificity in targeting. To address the larger problem of potential toxicity, peptides and conjugates need to be subjected to cytotoxicity studies.

Similarly, in experiments between Peptide-1 and Peptide-4, BL21(DE3) cells were also used. Results from these experiments are shown in TABLE 1.

TABLE 1

Antimicrobial activity ($LC_{90}$) for peptides and their acetylated derivatives

| Peptide | $LC_{90}$ (µg/ml) | |
|---|---|---|
| | Free Peptide | Acetylated Peptide * |
| Peptide-1 | 2.23 | 94.40 |
| Peptide-4 | 0.15 | 1.49 |

The "*" denotes antimicrobial activities of acetylated peptides, which are based on results of single dataset, while values for the free peptides are calculated from triplicate data.

As can be seen, the increased positive charge of Peptide-4 resulted in increased antimicrobial activity relative to Peptide-1. Moreover, like the above experiments, acetylation of Peptide-4 resulted in a smaller decease in antimicrobial activity relative to Peptide-1. In fact, the potency demonstrated by acetylated Peptide-4 with a net charge of +5 is comparable to that of the parent peptide (Peptide-1), which has a charge of +7. This closeness suggests that the antimicrobial potency is not solely the result of net positive charge. It also reflects distribution of charge, as well as possibly subtle influences associated with the acetylation of lysine side chains.

These peptides (Peptide-1, Peptide-2, Peptide-3 and Peptide-4) and their acetylated derivatives are intended to probe the significance of charge, degree of substitution and the C-terminal carboxyl group as they relate to the performance of the peptide and analogous antibiotic-CAMP conjugates. Peptide-2 and Peptide-3 serve as intermediates between Peptide-1 and Peptide-4 and are further intended to isolate the influence of the C-terminal carboxylic group in the antimicrobial activity of the acetylated/acylated peptide.

The performance of these peptides and their acetylated derivatives against K-12 *E. coli* in antimicrobial assays have provided insights into how the charge of the acetylated peptide impacts its potency and how great a loss of charge may be accommodated without compromising potency. It is also significant to note that none of the free or acetylated peptides demonstrate significant hemolytic activity, which suggests that it may be possible to engineer drug-peptide conjugates that specifically target invading bacteria using these peptides as carriers. Therefore, antibiotic-CAMP conjugates may be prepared that incorporate these peptides and either chloramphenicol or levofloxacin. Furthermore, the cytotoxicity of the peptides and their derivatives may be determined using cultured hepatocytes and measuring the release of lactate dehydrogenase. This measurement may be achieved by using, for example, the Cytotox96 kit (by Promega Corp. of Madison, Wis.), which is a well established method of measuring cytotoxicity. Antimicrobial studies using these peptides and their derivatives may be expanded to include nonvirulent or attenuated strains of *Francisella tularensis, Bacillus anthracis, Pseudomonas aeruginosa* and *Vibrio cholera*, among others as models for the disease causing organisms.

Furthermore, the performance of these peptides (Peptide-1, Peptide-2, Peptide-3 and Peptide-4) and their derivatives may be used in the design of a second generation of peptides employing the design criteria as described above. The performance of the antibiotic-CAMP conjugates may also be incorporated in the design process. In turn, the design process may be repeated with successive generations of peptides and peptide conjugates. Should none of the peptide conjugates based on Peptide-1, Peptide-2, Peptide-3 and Peptide-4 exhibit satisfactory antimicrobial activity against the selected panel of microbes or pass the hemolytic and cytotoxicity assays, it may be necessary to explore using alternative peptide scaffolds, such as full-length β-defensins or cathelicidins. The β-defensin or cathelicidin would provide the basis for the design of new smaller peptides to identify minimal elements required to generate conjugates that demonstrate satisfactory antimicrobial activity and minimal hemolytic activity.

B. Identification and Conjugation of Antimicrobial Agents

1. Chloramphenicol and Levofloxacin

As an embodiment, antibiotic-CAMP conjugates incorporate chloramphenicol and levofloxacin. Both are broad-spectrum antibiotics whose molecular structures contain functional groups that allow their attachment to linker segments through the formation of an ester bond, providing for the release of the drugs by hydrolysis of the ester bond. Additionally, the linker segment supplies a way of affixing the drug-linker adduct to the delivery vehicles through the acylation of primary amino groups (e.g., on the N-terminus and Lys side chains) present on the peptides. Alternatively, levofloxacin may be directly attached to the delivery peptide through the acylation of primary amino groups and hydroxyl groups (i.e., Ser side chains) present in the peptide.

Reaction conditions, such as reaction times, solvents and stoichiometry can be optimized to maximize yield and purity. These antibiotics may be used in the first generations of drug-peptide conjugates to evaluate and refine conjugate performance.

a. Chloramphenicol

Chloramphenicol is a well-characterized antibiotic with precedent for its conjugation to filamentous phage for specific targeting of *Staphylococcus aureus*. The drug exerts a bacteriostatic effect against both gram-positive and gram-negative bacteria by binding to the 50S ribosomal subunit and inhibiting protein biosynthesis. Chloramphenicol is relatively hydrophobic and attachment of Chloramphenicol to the carrier peptide can significantly alter its overall character and selectivity in targeting. Therefore, the degree of loading and positioning of attachment points may be important for the performance of chloramphenicol-peptide conjugates.

Referring to FIG. 11, the chloramphenicol-linker adduct may be prepared using a known protocol. In this process, chloramphenicol and a molar excess of glutaric anhydride are dissolved in a minimal volume of anhydrous tetrahydrofuran. A molar excess of triethylamine and a catalytic amount of dimethylaminopyridine are then added to the solution. The reaction can then be allowed to stir under nitrogen overnight at room temperature. The desired adduct is isolated from the reaction mixture by flash chromatography.

b. Levofloxacin

Levofloxacin is a third generation fluoroquinolone antibiotic that is effective against both gram-positive and gram-negative bacteria. Like other fluoroquinolones, such as ciprofloxacin, levofloxacin is usually bactericidal exerting antimicrobial effect by binding DNA gyrase and topoisomerase IV and interfering with DNA replication. While there is no precedent for the conjugation of levofloxacin to peptides and proteins, the carboxyl group present in levofloxacin provides a convenient way for conjugation. Unlike chloramphenicol, the N-substituted piperazine group present in levofloxacin provides two protonatable tertiary amino groups, which may help to offset the loss of primary amino groups on the peptide carrier, which is associated with drug conjugation.

Figure 12:
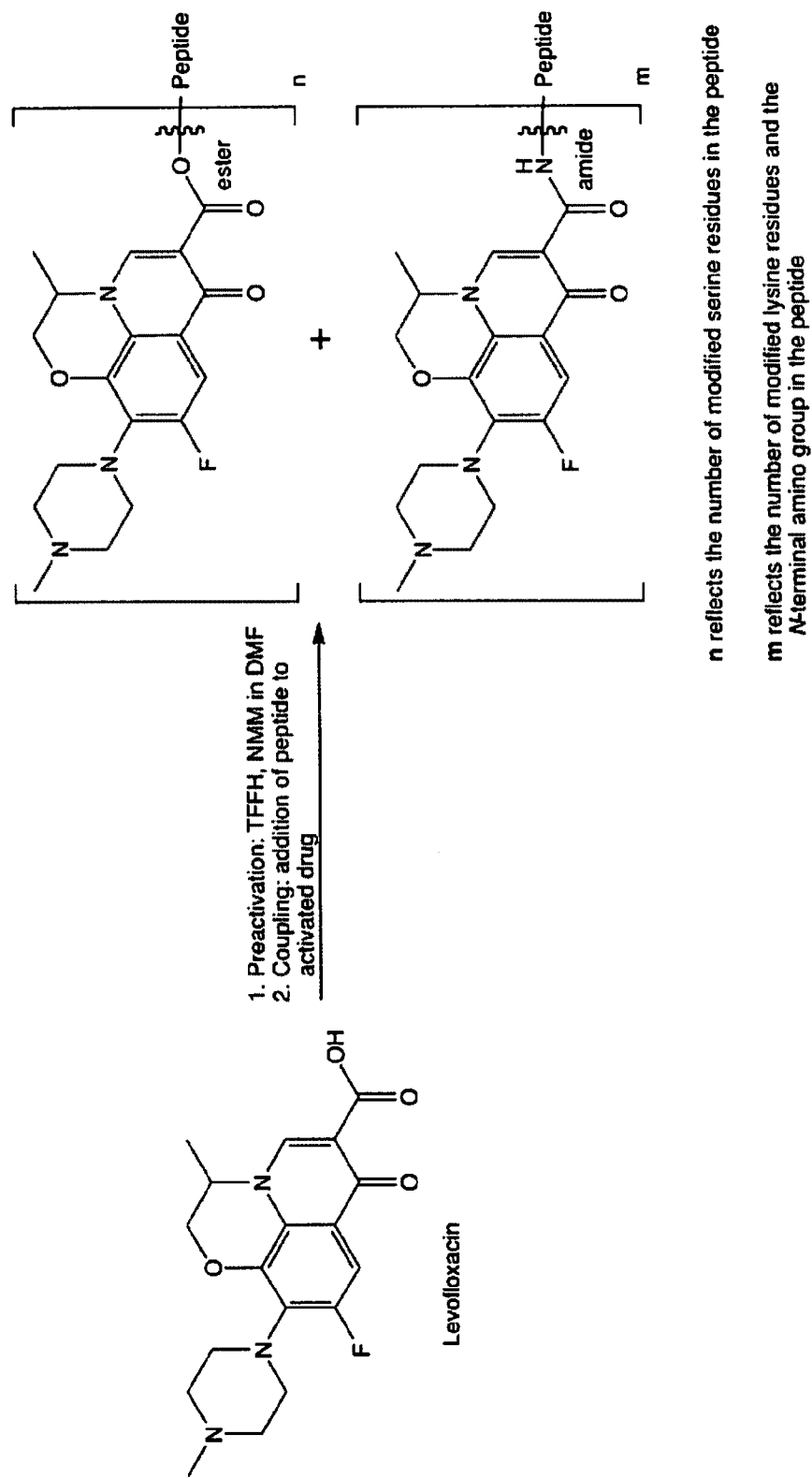
FIG. 12 illustrates direct attachment of levofloxacin to a peptide.

As shown in FIG. 12, levofloxacin may be directly attached to the peptide via its carboxylic acid group and direct acylation of amino and hydroxyl groups present in the peptide. Such process involves fewer synthetic and purification steps than would be required for the strategy described below, which involves the use of a linker. It may also avoid the need for isolation of the conjugate by chromatographic methods.

Figure 13:
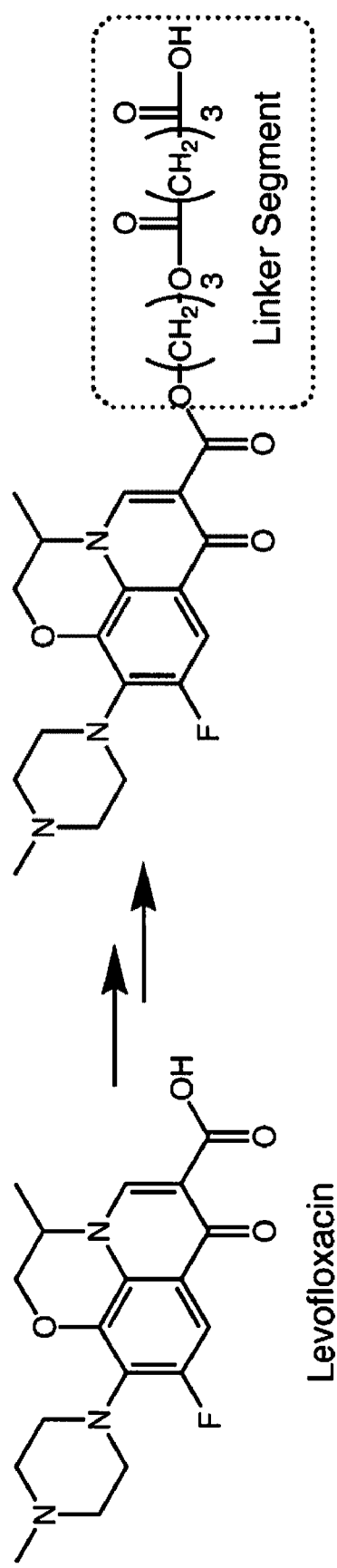
FIG. 13 shows levofloxacin and the levofloxacin-linker adduct.

Alternatively, a strategy could be employed where the levofloxacin molecule is connected to the peptide via a linker segment. As shown in FIG. 13, assembly of the levofloxacin-linker adduct is a two-step process. In the first synthetic step, 1,3-propanediol may be affixed to the carboxylic acid of levofloxacin. This affixation may be accomplished by preactivating the carboxyl group using N,N'-dicyclohexylcarbodiimide (DCC) and hydroxysuccinimide. The activated levofloxacin may then be combined with a large molar excess of 1,3-propanediol, triethylamine, and a catalytic amount of dimethylaminopyridine. This combination is allowed to stir under nitrogen, with progress of the reaction being monitored by reversed-phase high performance liquid chromatography (HPLC). Once the reaction has reached completion, the levofloxacin-linker adduct can then be assembled with the addition of a glutarate group using reaction conditions similar to those described for generating the chloramphenicol-linker adduct.

c. Conjugation

Antibiotics bearing carboxyl groups or other suitable functional groups may be attached directly to the carrier peptide via acylation. With simple and unstructured peptides, it may be possible to preactivate carboxyl groups on the drug molecules and carry out the acylation reaction in organic solvents (such as dimethylformamide) instead of aqueous conditions, which may improve conjugation efficiency.

Alternatively, the antimicrobial agent may be connected to the peptide via antibiotic-linker adducts. In such cases an antibiotic-linker adduct may need to be prepared. If so, once the antibiotic-linker adducts have been prepared, they may be conjugated to antimicrobial peptides. In conjugating the adducts to the peptide, the carboxylic acid of the linker is initially activated by forming the succinimido-ester. The succinimido-ester may be generated by treating the antibiotic-linker adduct with DCC in the presence of a molar excess of N-hydroxysuccinimide. Reaction completion can be monitored by thin-layer chromatography or reversed-phase HPLC.

After the reaction is completed, the reaction mixture may be filtered to remove the dycyclohexyl urea byproduct that is formed in the course of the reaction. If necessary, the activated antibiotic-linker adduct may be purified by flash chromatography. This type of strategy is common for forming activated esters that may be used to couple with peptides and proteins under mild aqueous conditions.

The antibiotic-linker adducts may be conjugated to free amino groups on the carrier CAMP using known protocols for the coupling of chloramphenicol to filamentous phage. The peptide may first be dissolved in aqueous buffer (at a pH of about 8.5). A molar excess of the activated antibiotic-linker adduct may then be dissolved in a minimal volume of tetrahydrofuran, dimethylsulfoxide, or other water miscible organic solvent. The solution containing the activated antibiotic-linker may then be added to the aqueous peptide solution. The conjugation reaction may be allowed to stir at room temperature with progress of the reaction monitored by reversed-phase HPLC.

It may be necessary to alter reaction conditions (such as solvent, coupling reagent, temperature, and drug/peptide stoichiometry) to maximize conjugation efficiency. A greater molar excess of antibiotic and coupling reagent or longer reaction times may also be required to achieve efficient loading.

As a representative protocol, the following example describes how a conjugate can be formed through direct acylation and subsequently be purified. In this example, a levofloxacin conjugate is formed. A reaction vessel may be dried in an oven for ~30 minutes and then allowed to cool to room temperature under nitrogen. Tetramethylfluoroformamidinium hexafluorophosphate (TFFH, 36.5 mg, 0.23 mmol) and levofloxacin (50 mg, 0.14 mmol) are weighed and subsequently dissolved in dry dimethylformamide (DMF, 200 µl). The solution is transferred to the dry reaction vessel, and the mixture is allowed to stir under nitrogen at room temperature. A catalytic amount of N,N-dimethylaminopyridine (DMAP) is then added to the solution followed by 4-methylmorpholine (60 µl, 0.54 mmol). Additional DMF (~500 µl) is added to dissolve any solids that may be present and the activation reaction allowed to stir at room temperature under nitrogen for ~1 hour. After which, the reaction is charged with peptide (Peptide-4, mw 2190 g/mole as TFA salt, 2 mg, 0.00091 mmol), and allowed to stir overnight at room temperature under nitrogen. The following morning, the reaction mixture is diluted into diethyl ether (50 ml), and the resulting precipitate pelleted by centrifuging at 5000 RPM for 10 minutes. The supernatant is removed and the pelleted material transferred to a 1.5 ml microcentrituge tube. Residual ether is then removed using a speed-vac. The dried pellet is then resuspended in water (1 mL) and then pelleted. The supernatant is collected. The pelleted material is again suspended in water (1 mL) and centrifuged. The supernatant from the second is combined with the first and the solution is dialyzed (1000 MWCO membrane) with water (3 L) at 4° C. for two days. Over the two day period, the dialysate is changed twice times. After dialysis the sample is lyophilized to dryness and stored at −20° C. until used or characterized.

Figure 14:
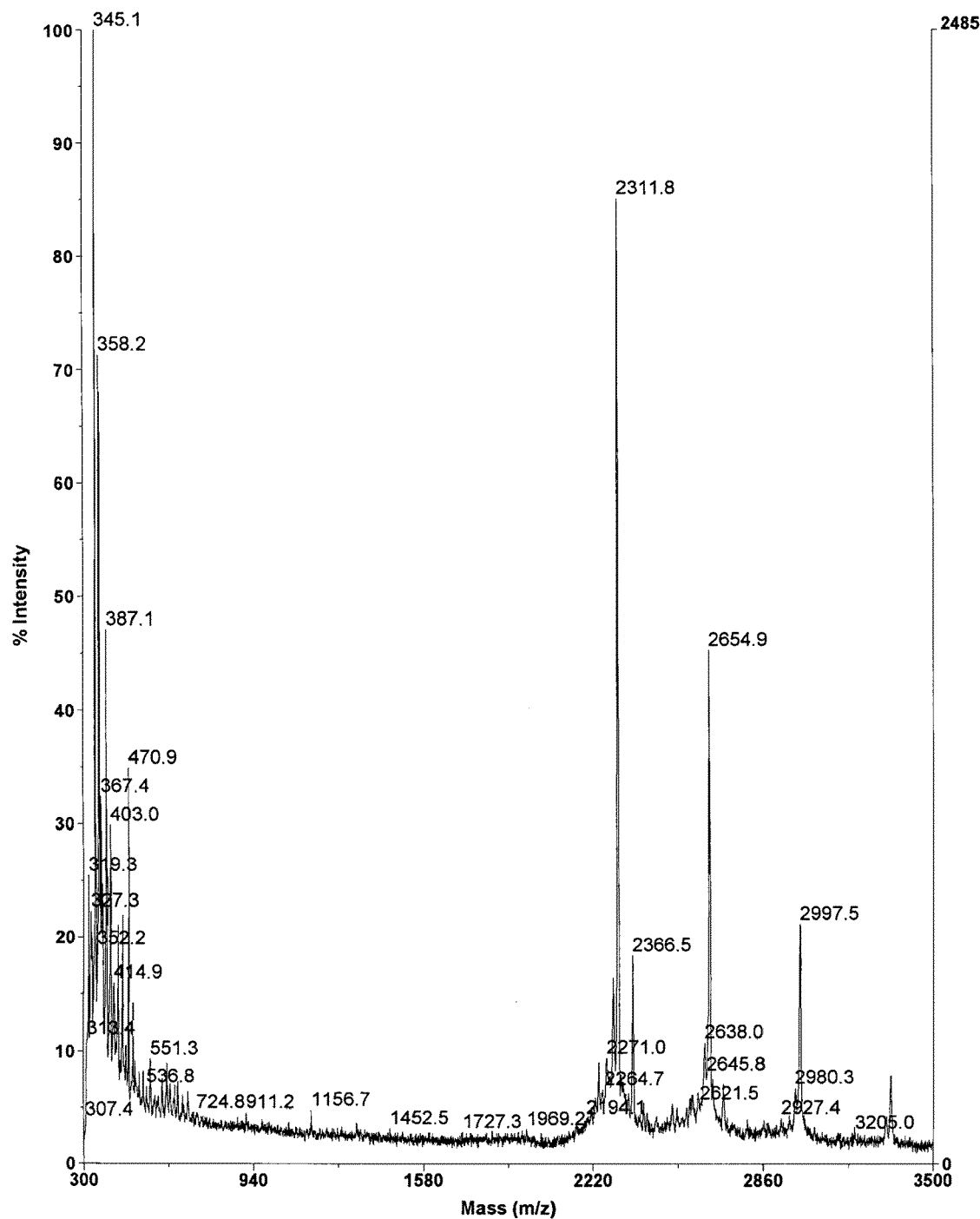
FIG. 14 shows an example of MALDI-TOF spectra of levofloxacin conjugates.

The degree of conjugation may be evaluated by MALDI-TOF mass spectrometry. An example of MALDI-TOF spectra of levofloxacin conjugates is depicted in FIG. 14. The molecular weight for the number of levofloxacin groups can be summarized as follows: 1285.5 for 0 levofloxacin groups; 1628.87 for 1 levofloxacin group; 1972.24 for 2 levofloxacin groups; 2315.61 for 3 levofloxacin groups; 2658.98 for 4 levofloxacin groups; and 3002.35 for 5 levofloxacin groups.

Figure 15:
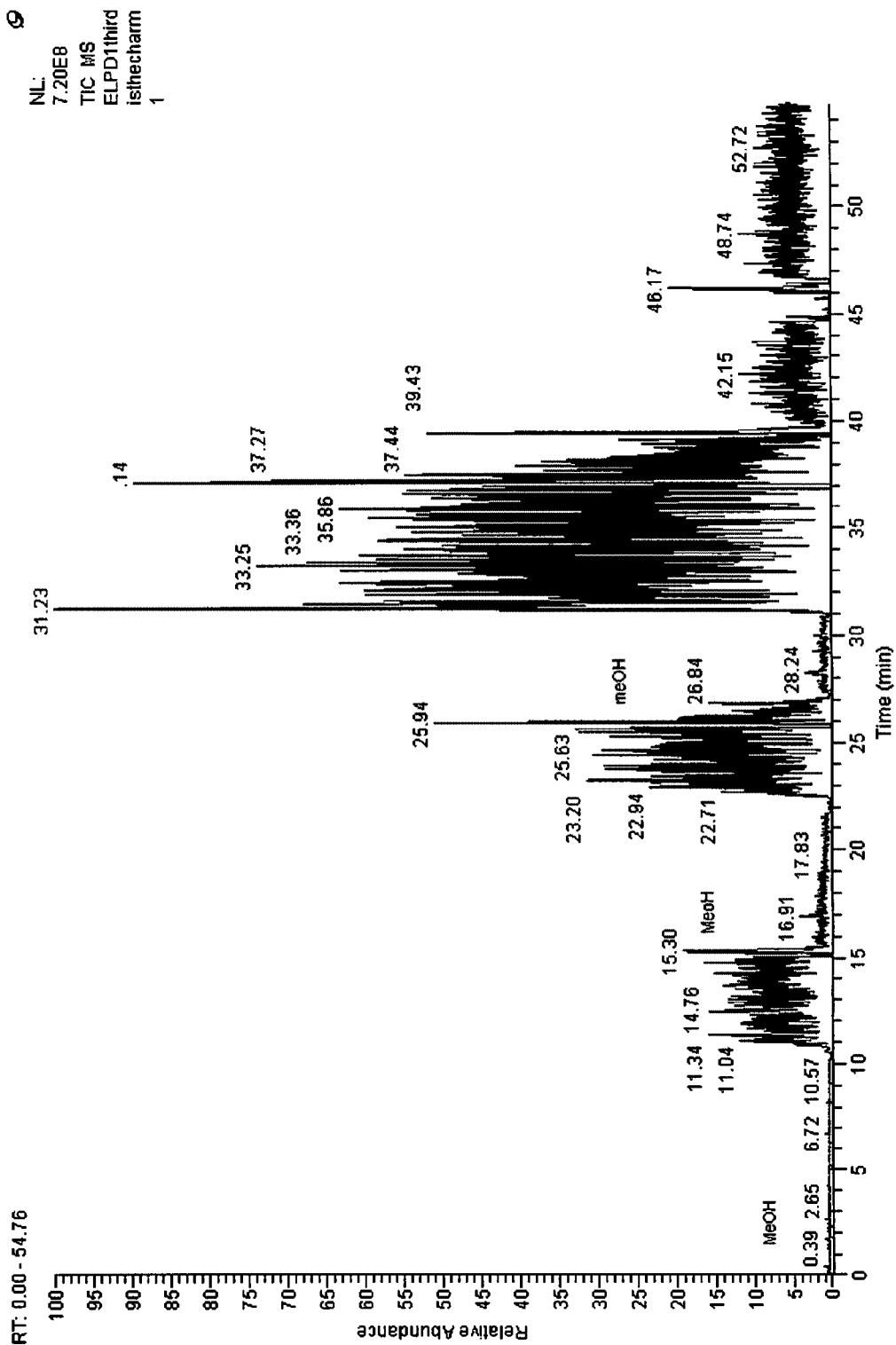
FIG. 15 shows an example of LC calibration curve for levofloxacin in solution and analysis of conjugates for the presence of free levofloxacin.

Conjugates containing 4 or 5 levofloxacin molecules reflect acylation of Ser residues, as well as the Lys residues and the N-terminal amino group. In addition, analysis of prepared levofloxacin-peptide conjugates for the presence of free levofloxacin using HPLC, along with reference levofloxacin concentrations are shown in FIG. 15. This data indicates that no significant amounts of free levofloxacin are present in the prepared conjugate.

The performance of levofloxacin-Peptide-4 conjugates prepared as described above have been evaluated against K-12 E. coli. In these assays, it was found that the Peptide-4 conjugates demonstrated an impressive $EC_{50}$ of 0.042 µg/ml, which represents a potency of ~30× that of the unmodified peptide, as determined earlier. The results of these assays are given in FIG. 16.

As for the assay conditions used for the conjugate: the E. coli and the conjugate were incubated in LB. The potencies reported for the parent peptide (Peptide-4) were determined by incubating the bacteria and the peptide in 10 mM phosphate. The latter conditions represent a much more ideal environment for CAMP antimicrobial effectiveness than that used in evaluating the conjugate. Thus the actual superiority in the potency of the conjugate over the free peptide is likely much greater than the observed 30 fold increase.

2. Diazeniumdiolates and Conjugation

Figure 17:
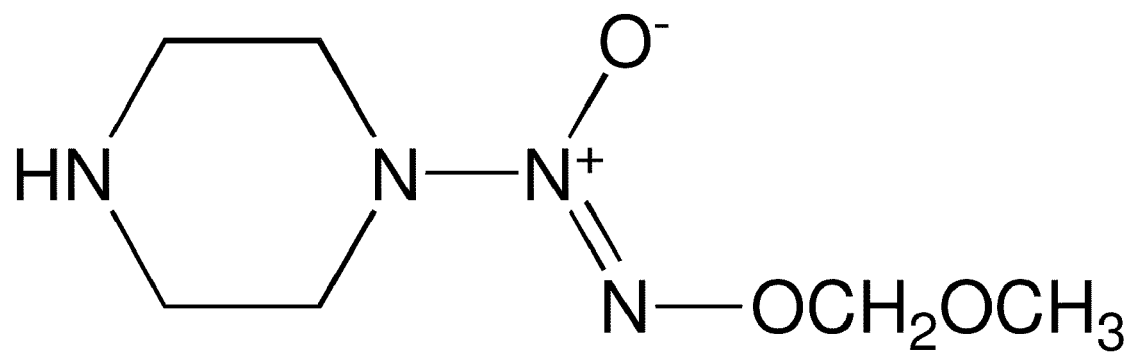
FIG. 17 shows methoxymethyl-protected monodiazeniumdiolate of piperazine.
Figure 18:
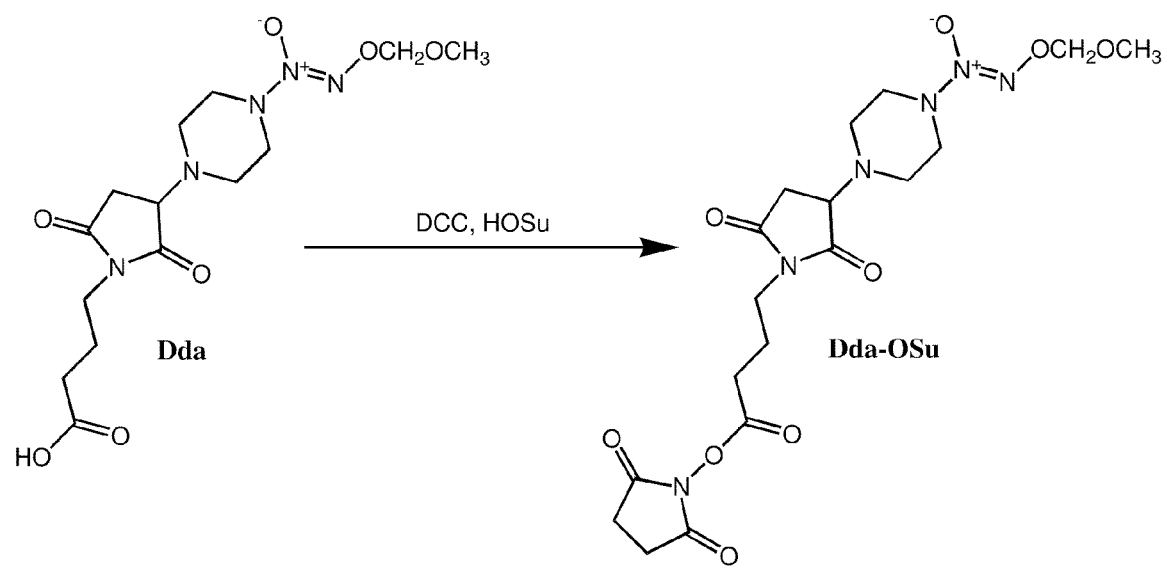
FIG. 18 shows the succinimido ester (Dda-OSu) is prepared by treating Dda with dicyclohexylcarbodiimide (DCC) and N-hydroxysuccinimide (HOSu).

Diazeniumdiolate-peptide conjugates can be created using the methoxymethyl-protected monodiazeniumdiolate of piperazine, as shown in FIG. 17, as the NO source. Synthetic procedures, by which the bifunctional amine piperazine can be used for attaching the diazeniumdiolate functional group into a variety of biomedically useful molecules, have been previously described. A derivative of this diazeniumdiolate was conjugated to human and bovine serum albumin using an asymmetric maleimidobutyric acid linker. A similar approach can be used to conjugate diazeniumdiolate groups to the proposed peptide carriers. In this approach, the monodiazeniumdioloate of piperazine is linked to maleimidobutyric acid to produce the diazeniumdiolate acid (Dda,) shown in FIG. 18. Activation of the carboxylic acid by forming the succinimido ester (Dda-OSu) allows for the diazeniumdioalte group to be conjugated through the acylation of primary amino groups present on the unprotected peptide under mild conditions.

Dda may be incubated in phosphate buffer (at a pH of about 7) to determine its stability to these conditions. Similarly, Dda stability may be evaluated under antimicrobial and hemolytic assay buffer conditions. NO release may be monitored during antimicrobial and hemolytic assays to determine whether cellular processes result in accelerated release of NO in either free Dda or the Dda-peptide conjugates.

In these experiments, the breakdown and release of NO may be monitored using standard specrophotometric oxyhemoglobin assays, where changes to the Soret band (at about 401 nm) are used to detect the NO-mediated conversion of oxyhemoglobin to methemoglobin. This method is generally used for the quantitative detection of NO at micromolar levels.

Initial antimicrobial activities of the Peptide-1 have been evaluated against *E. coli* BL21(DE3). The antimicrobial activities of free peptides, diazeniumdiolates, and diazeniumdiolate-peptide conjugates may be evaluated against selected microbes, such as K-12 *E. coli, Staphylococcus aureus*, and *Shigella dysentariae*. The work represented in current literature and the present invention's results indicates that the parent peptide demonstrates good antimicrobial activity against *E. coli*, but may be less potent against other microbes, such as *Staphylococcus aureus, F. tularensis*, and *A. actinomycetemcomitans*. NO has been reported to be potent against *Staphylococcus aureus*, but possibly not as effective against *E. coli*. Therefore, these microbes may provide a way of evaluating the performance of the conjugate with respect to both components, the peptide and the diazeniumdiolate. *Shigella dysentariae* has been included to evaluate the performance of the conjugates against an actual enteric pathogen.

C. Evaluation and Refinement of Conjugates

To gain basic insights into how performance of the peptides relates to that of the corresponding antibiotic-CAMP conjugates, the first generation of chloramphenicol and levofloxacin conjugates may be prepared utilizing all four of the initial peptides (Peptide-1, Peptide-2, Peptide-3 and Peptide-4). These conjugates may be subjected to the full battery of antimicrobial, hemolytic, and cytotoxicity assays to evaluate their performance, which in turn may be compared to that of the free and acetylated peptides and the free drugs.

The performance of the first generation of antibiotic-CAMP conjugates and the insights gained from their analysis may be utilized in the design of the next generation of free peptides to be evaluated. The following generations of conjugates may be generated based on those second-generation peptides that demonstrated superior performance in the antimicrobial, hemolytic and toxicity assays as both the free peptides and acetylated derivatives. This process may be repeated, each time selecting for those peptides and antibiotic-CAMP conjugates that demonstrate superior performance. Due to differences in the physical properties of different antibiotics, it may be necessary to consider each one separately in the revision process.

In addition to evaluating the antimicrobial potency of the antibiotic-CAMP conjugates, the release of free drug from the conjugates under conditions used in the various activity assays may also be evaluated. Conjugates may be incubated in water, phosphate buffered saline, and the buffers used in the antimicrobial, hemolytic and cytotoxicity assays. Drug release may be monitored by HPLC or LC-MS. Drug release may also be monitored under actual assay conditions. The results of these studies may be correlated with the performance of the conjugate in antimicrobial, hemolytic and cytotoxicity assays. The information provided by these drug-release studies may be utilized in the design of future conjugates, with a particular focus on the nature of the bond that connects the drug to the peptide and/or to the linker segment, if present, as well as the nature of the linker segment (if one is used). Whether linker segments are present or are being used, the linkers can be long (e.g., succinate) or short (e.g., glutarate). Also, ester bonds may be used in place of amid bonds to achieve this goal.

An advantage of the proposed antibiotic-CAMP conjugate strategy is that it employs a modular approach to assembling the conjugate. This approach tends to allow significant flexibility and the ability to adjust the constructs in response to their performance in the various assays.

III. Experiments

In one embodied experiment, the materials used include peptides that were custom synthesized by CelTek Bioscience, LLC (Nashville, Tenn.) or by Genscript Corporation (Piscataway, N.J.) using Fmoc chemistry, K12 *E. coli*, ATCC #25404 (American Type Culture Collection, Manassas, Va.), and horse erythrocytes (Hemasource, Inc., Eugene, Oreg.). Mass-spectra may be collected on a prOTOF 2000 (PerkinElmer, Inc., Waltham, Mass.).

A. Peptide Acetylation

Acetylation reagent may be prepared by combining ~200 µl of acetic anhydride with ~600 µl of methanol. Using any of the above described peptides, the peptide (~2-~2.5 mg) may be reconstituted in ~200 µl of ~50 mM ammonium bicarbonate buffer. About 500 µl of the acetylation reagent may then be added to the peptide solution. The reaction may be left at room temperature for about 1 hour. Methanol and unreacted acetic anhydride may then be removed with the aid of a speed-vac. The remaining aqueous solution may then be lyophilized to dryness.

In the case of each peptide, analysis of the resulting solid by MALDI-TOF may indicate that the isolated material consisted of fully acetylated peptide, without detectable amounts of intermediate acetylated species being present. This protocol is based on a protocol reported by IonSource for the acetylation of peptides and proteins.

B. Antimicrobial Activity Assay

The antibacterial activities of the free and acetylated peptides may be determined using K12 *E. coli* and a known assay protocol. Bacteria may be incubated in Luria Bertani broth at 37° C. until reaching an $OD_{600}$ of 0.8-1.1. Cell density may be monitored using optical density at 600 nm. Cells were then diluted to a concentration of $10^6$ CFU/ml in ~10 mM sodium phosphate (pH ~7.5), containing varied concentrations of peptide or acetylated peptide. Peptide concentration used in the assays may range from 0 µg/ml to ~100 µg/ml with intermediate concentrations varied for each peptide in order to maximize the number of data points in or near the transition region.

Assay cultures may be incubated at 37° C. for about two hours. Afterwards, serial dilutions of each assay culture may be prepared and then plated in triplicate onto Luria Bertani broth plates. The plates may be incubated at 37° C. overnight (~16 h). Colonies may be counted the following morning.

Bacterial survival at each peptide concentration may be calculated according to the ratio of the number of colonies on the plates corresponding to the peptide concentration and the average number of colonies observed for assay cultures lacking peptide. The peptide concentration required to kill ~50% of the viable *E. coli* in the assay cultures ($EC_{50}$) may be determined by plotting percent survival as a function of the log of peptide concentration (log µg/ml) and fitting the data, using GraphPad Prism (GraphPad Software, Inc., San Diego, Calif.), to Equation (1), which describes a sigmoidal dose-response.

$$S = S_B + \frac{(S_T - S_B)}{1 + 10^{(LogEC_{50} - X)H}}. \quad (1)$$

In Equation (1), S is percent survival, $S_T$ and $S_B$ represent the upper and lower survival boundaries, X is the log of the peptide concentration, and H is the Hill slope of the transition region. Results of these assays are given in FIG. 19 and TABLE 2.

Figure 19:
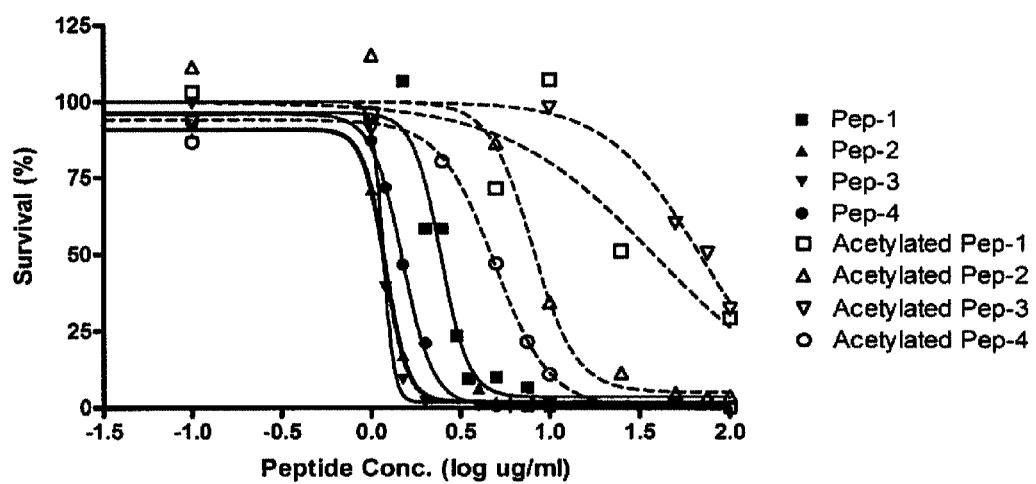
FIG. 19 shows an example of the antimicrobial activity for Pep-1, Pep-2, Pep-3, Pep-4 and their acetylated derivatives.

In particular, FIG. 19 plots bacterial survival as a function of free or acetylated peptide concentration (log µg/ml) for each peptide and acetylated derivative.

TABLE 2

Antimicrobial potency for each peptide and acetylated peptide against *E. coli*.

| | Antimicrobial Activity ($EC_{50}$, µg/ml) | |
|---|---|---|
| Peptide | Free * | Acetylated * |
| Pep-1 | 2.4 (2.2-2.7) | ~40‡ |
| Pep-2 | 1.2 (1.1-1.3) | 8.1 (6.5-9.9) |
| Pep-3 | 1.2 (1.1-1.2) | ~70‡ |
| Pep-4 | 1.5 (1.4-1.6) | 4.9 (4.2-5.8) |

The $EC_{50}$ values for each derivative in TABLE 2 may be determined by fitting data into Equation 1.
The symbol "*" denotes values, given in parentheses, that fall in the 90% confidence range.
The symbol "‡" denotes estimated $EC_{50}$ values for acetylated Pep-1 and acetylated Pep-3; no error range is given.

In fitting the data for all peptides and acetylated peptides (except acetylated Pep-1 and acetylated Pep-3), $S_T$ and $S_B$ may be restricted to values ≦100% and ≧0% respectively. For acetylated Pep-1 and acetylated Pep-3, the absence of data points defining the lower boundary necessitated that $S_B$ be set to 0% in order to fit the data to Equation (1) and provide an estimated $EC_{50}$ for these peptides.

C. Hemolysis Assay

Hemolytic activities of the free and acetylated peptides may be determined using horse erythrocytes, in an assay adapted to a microtitre plate format. Cells may be prepared by centrifuging ~1 ml of horse erythrocytes at 1620×g, and then resuspending the pelleted cells in ~1 ml of 1× Dubelco's phosphate-buffered saline (Dubelco's PBS, Mediatech, Manassas, Va.). The cells may then be pelleted again. The process may be repeated (e.g., three more times). Following the final wash, the cells may be resuspended in ~0.750 ml of PBS. Approximately two hundred microliters of washed erythrocyte suspension may then be diluted into ~9800 µl of PBS to afford about 2% suspension. Aliquots of sterile water, peptide, and Dubelco's PBS may then be combined in the wells of a 96 well microtitre plate so as to provide a gradient of peptide concentrations (0, ~0.1, ~1, ~10, ~100, and ~1,000 µg/ml), to which the ~2% erythrocyte may be added. The assay solutions may then be incubated at 37° C. for ~1 hour. An additional ~100 µl of phosphate buffer may then be added to each well. The microtitre plate may be centrifuged at 1000×g for about 2 minutes to pellet cells and debris. An aliquot of supernatant (~150 µl) from each well may then be transferred to a fresh microtitre plate, and the absorbance at ~540 nm (heme) may be obtained for each solution. The percent hemolysis may be calculated based on the ratio of the absorption of supernatants from wells containing peptide and the absorption of supernatants from wells containing no peptide. In both cases, the recorded absorption may be adjusted for the background absorption of the plates.

D. Experimental Results

Referring to TABLE 3, a series of peptides has been designed to test the effect of net charge and charge distribution on antimicrobial activity. In particular, the table shows aligned amino acid sequences of Pep-1, Pep-2, Pep-3, and Pep-4. The Pep-1 variant is equivalent to the decapeptide described in current literature. In the Pep-2 variant, an Arg residue has been substituted for Lys4. In the Pep-3 variant, the C-terminal carboxyl group of Pep-1 has been replaced with a carboxamide group, which effectively eliminates the only acidic group in the peptide. The Pep-4 variant combines both sequence changes.

The underlined residues indicate the serine residues that have been substituted for the cysteine residues present in the hBD-3 parent sequence. The substituted arginine residue at the fourth position in the sequences of Pep-2 and Pep-4 is in bold. Similarly, the C-terminal carboxamide in Pep-3 and Pep-4 is indicated by the italicized "—$NH_2$". Nominal charges for the free and acetylated peptides at a pH of 7 are also given.

TABLE 3

| | Aligned Amino Acid Sequences | | |
|---|---|---|---|
| | | Charge at pH = 7 | |
| Peptide | Amino Acid Sequence | Free | Acylated |
| Pep-1 | RGRK<u>SS</u>RRKK (SEQ ID NO. 2) | +7 | +3 |
| Pep-2 | RGRR<u>SS</u>RRKK (SEQ ID NO. 3) | +7 | +4 |

TABLE 3-continued

Aligned Amino Acid Sequences

| Pep-tide | Amino Acid Sequence | Charge at pH = 7 Free | Acylated |
|---|---|---|---|
| Pep-3 | RGRK<u>SS</u>RRKK-NH$_2$ (SEQ ID NO. 5) | +8 | +4 |
| Pep-4 | RGRR<u>SS</u>RRKK-NH$_2$ (SEQ ID NO. 6) | +8 | +5 |

Acetylated derivatives of all four peptides may be prepared to expand and evaluate the range of peptide net charges and charge distributions. Unlike the majority of CAMPs, the Pep-1 sequence does not contain strongly hydrophobic residues, such as leucine, isoleucine, valine, tryptophan, or phenylalanine. However, the side chains of lysine and arginine residues themselves are amphipathic, with positively-charged amino and guanidino groups, respectively, tethered to the peptide backbone by aliphatic chains. Acetylation of the primary amino groups present in the peptides, specifically the N-terminus and ε-amino groups of lysine residues, provides a means of neutralizing the charge associated with these groups, while retaining the hydrophobic and steric properties of the side chains of Lys residues. Therefore, acetylated derivatives of the four peptides may be prepared to further evaluate how positively-charged groups may contribute to potency in these small antimicrobial peptides.

The antimicrobial potencies of the free and acetylated peptides may be evaluated using K12 *E. coli* and plotting bacterial survival as a function of peptide concentration. FIG. 19 highlights this graphical representation. Here, the antimicrobial activity for Pep-1, Pep-2, Pep-3, Pep-4, and their acetylated derivatives is illustrated by plotting bacterial survival as a function of free or acetylated peptide concentration (log µg/ml) for each peptide and acetylated derivative.

$EC_{50}$ values for each peptide and peptide derivative may be calculated by fitting data to Equation (1), which defines standard sigmoidal dose response behavior. This equation allows for a variable Hill slope.

The unmodified peptides demonstrated similar antimicrobial potencies, with free Pep-1 being slightly less potent than Pep-2, Pep-3, and Pep-4. This trend may be reflected in the calculated $EC_{50}$ values for the free peptides. As indicated in TABLE 2, Pep-2 and Pep-3 each may have an $EC_{50}$ of ~1.2 µg/ml, and Pep-4 may have an $EC_{50}$ of ~1.5 µg/ml. The 95% confidence ranges associated with each of these values tend to suggest that the differences in potency between Pep-1 and the other free peptides likely reflect actual differences in potency. The acetylated peptides demonstrated more varied potencies, consistent with the larger range of charges (+5 to +3). Acetylated Pep-4 with a charge of +5 may have an $EC_{50}$ of ~4.9 µg/ml, and acetylated Pep-2 with a charge of +4 may have an $EC_{50}$ of ~8.1 µg/ml, making them only slightly less potent than free Pep-1 (~50% and ~25%, respectively).

However, acetylated Pep-1 and Pep-3 may demonstrate detectable antimicrobial activity only at very high peptide concentrations. Neither acetylated peptide killed more than ~80% of bacteria within the range of evaluated peptide concentrations. Therefore, the $EC_{50}$ values given for acetylated Pep-1 and Pep-3 (~39 µg/ml and ~70 µg/ml, respectively) generally represent estimated values. Significant error is associated with both.

Figure 20:
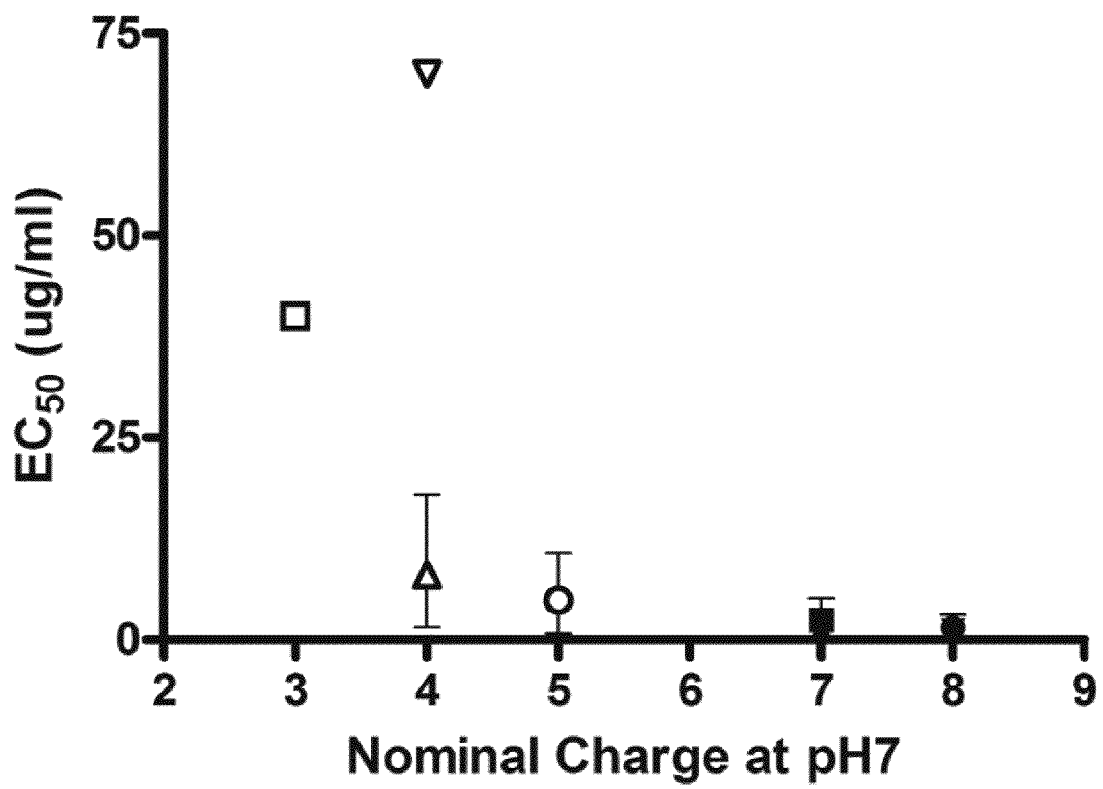
FIG. 20 shows antimicrobial potency ($EC_{50}$) of the four decapeptides and their acetylated derivatives as a function of nominal charge at pH 7.

Referring to FIG. 20, the importance of positive charge, as well as its impact on antimicrobial potency, is evident when $EC_{50}$ values are plotted as a function of peptide charge. This figure shows antimicrobial potency ($EC_{50}$) of the four decapeptides and their acetylated derivatives as a function of nominal charge at pH ~7. The free peptides, with charges of +8 and +7, are the most potent and demonstrate very similar potencies. Acetylated Pep-4, with a charge of +5, tends to be only slightly less potent than the unmodified peptides. The potency of acetylated Pep-1, with a charge of +3, is ~5% of the free peptide, which has a charge of +7. While the potencies of peptides with a charge of +4 (namely, acetylated Pep-2 and Pep-3) are much lower than their unmodified counterparts, the degree to which their potency is diminished appears to be peptide dependent.

As expected, antimicrobial potency diminishes as peptide charge is decreased. Going from a formal charge of +8 to +5 resulted in a relatively small decrease in potency ($EC_{50}$ 1.2→4.9 µg/ml). Larger decreases in potency can be observed for peptides with nominal charges of less than +5, with the peptide with the least positive charge (acetylated Pep-1 with a nominal charge of +3) demonstrating an $EC_{50}$ of ~39 µg/ml, approximately a sixteen fold decrease in potency relative to free Pep-1 with a nominal charge of +7. Acetylated Pep-2 and Pep-3 both had a nominal charge of +4, but they tend to demonstrate very different antimicrobial potencies, with a nearly 10-fold difference in their $EC_{50}$ values (8.1 and ~70 µg/ml respectively).

The dramatic difference in the antimicrobial potencies demonstrated by acetylated Pep-2 and Pep-3 is interesting. These acetylated peptides achieve their nominal +4 charge by different means. In acetylated Pep-2, Lys4 may be replaced with an Arg residue, which can result in the peptide having one less acetylation site. Such replacement helps preserve the positive charge at this position in the acetylated peptide.

In contrast, acetylated Pep-3 generally retains all of the available acetylation sites (primary amino groups) that are present in Pep-1. But, the C-terminal carboxyl group may be been replaced with a C-terminal amide. This function effectively eliminates the only group present in the peptide with a negative charge at pH ~7.5. The fact that these peptides display such different antimicrobial potencies suggests that features other than nominal net charge play a significant role in their antimicrobial effectiveness, at least in peptides with intermediate charges.

While their acetylated counterparts display dramatically different antimicrobial potencies, free Pep-3 and Pep-2 demonstrate nearly identical antimicrobial potencies, despite the fact that Pep-3 has a nominal charge that is +1 greater than Pep-2 (+8 and +7 respectively). Such potency characteristic suggests that derivatives/variants of Pep-1 with intermediate charges tend to be more sensitive to mechanistic perturbation. The behavior of the free and acetylated peptides may provide insights into the antimicrobial mechanism employed by these peptides. The increased potency of acetylated Pep-2 relative to acetylated Pep-3 could reflect how differences in the distribution and number of charged groups between the two peptides impact the antimicrobial mechanism.

Acetylated Pep-2 generally contains five arginine residues. Each may contribute a positively-charged side chain, as well as a negatively-charged C-terminal carboxylic acid group. While acetylated Pep-3 may contain less arginine residues, it has a neutral C-terminal carboxamide in place of the carboxylic acid group present in Pep-2. Furthermore, it has been recently reported that substituting arginine residues for lysine residues in human alpha-defensin-1 (HNP-1) resulted in a significant increase in antimicrobial potency. It should be noted that this effect was not observed when similar substitutions were made in the sequence of hBD-1. According to the current literature, the potency difference observed for HNP-1 may be attributable in part to the fact that the guanidino group of arginine residues may interact with negatively charged and polar groups to a greater extent than can the primary amino group of the lysine side chain. Such interaction may impact how the peptide and the bacterial membrane interact with each other, and the overall antimicrobial effectiveness of the peptide.

The free decapeptides and their acetylated derivatives may be incubated with horse erythrocytes to evaluate their hemolytic activity, which is not an uncommon occurrence for antimicrobial peptides. The full-length hBD-3 and disulfide isoforms of the defensin have been reported to demonstrate significant hemolytic activity at elevated peptide concentrations. Additionally, other short peptides have been reported to demonstrate hemolytic activity.

A wider range of peptide concentrations was used in these assays, with conditions expanded to include peptide concentrations of up to ~1 mg/ml. In these assays, the free and acetylated peptides demonstrated no significant hemolytic activity at the concentrations used in evaluating antimicrobial activity (~0.1-~100 μg/ml). Results of these assays appear in FIG. 21. Specifically, hemolytic activity of (A) Pep-1, Pep-2, Pep-3, and Pep-4 and (B) acetylated Pep-1, Pep-2, Pep-3, and Pep-4 is shown. Absorbance at 540 nm was used to monitor the release of hemoglobin by horse erythrocytes that have been incubated with varied concentrations of free peptide or acetylated peptide.

Free Pep-1, Pep-2, Pep-3, and Pep-4 showed slight hemolytic activity (<~2%) at a concentration of ~1 mg/ml, and their acetylated counterparts showed no significant propensity to lyse erythrocytes even at this high concentration. These results suggest that the free and acetylated peptides attack bacterial cells, such as *E. coli*, at significantly lower concentrations than is required for them to demonstrate any effect against erythrocytes.

E. CONCLUSION

The performance of the free and acetylated peptides described here suggests that the relationship between their antimicrobial properties and peptide charge is more complex than merely being a function of net charge. This discovery is most evident in the performance of acetylated derivatives of Pep-2 and Pep-3. Both have nosminal net charges of +4, but they also demonstrate very different potencies. Whether the disparity in antimicrobial potencies displayed by these acetylated peptides is the result of differences in charge distribution in the peptides or the Arg/Lys substitution in Pep-2 is not clear. While it has been reported that hBD-3 disrupts membranes, the same may not be true for Pep-1 and the variants described herein. The lack of structure and short size suggest that their antimicrobial mechanism differs from that employed by full-length hBD-3. While these decapeptides do not readily fit into any of the commonly described structural classes, their sequences do resemble those of peptides associated with membrane translocation. Therefore, it is possible that these peptides may derive part of their antimicrobial potency by targeting internal systems. Meanwhile, it should be noted that it has been suggested that some CAMPs may also target external (non-membrane) and intracellular systems, which may contribute to their microbicidal activity. Furthermore, it has been reported that buforin II, a 21-residue CAMP, kills *E. coli* without lysing the bacterial membrane. Moreover, the peptide penetrated the bacterial membrane and that it bound both RNA and DNA in gel-retardation experiments.

The foregoing descriptions of the embodiments of the present invention have been presented for purposes of illustration and description. They are not intended to be exhaustive or be limiting to the precise forms disclosed, and obviously many modifications and variations are possible in light of the above teaching. The illustrated embodiments were chosen and described in order to best explain the principles of the present invention and its practical application to thereby enable others skilled in the art to best utilize it in various embodiments and with various modifications as are suited to the particular use contemplated without departing from the spirit and scope of the present invention. In fact, after reading the above description, it will be apparent to one skilled in the relevant art(s) how to implement the present invention in alternative embodiments. Thus, the present invention should not be limited by any of the above described example embodiments. For example, the present invention may be practiced over other animals (such as treatment of domestic animals in veterinary clinics).

In addition, it should be understood that any figures, graphs, tables, examples, etc., which highlight the functionality and advantages of the present invention, are presented for example purposes only. The architecture of the disclosed is sufficiently flexible and configurable, such that it may be utilized in ways other than that shown. For example, the steps listed in any flowchart may be reordered or only optionally used in some embodiments.

Further, the purpose of the Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the present invention of the application. The Abstract is not intended to be limiting as to the scope of the present invention in any way.

Furthermore, it is the applicants' intent that only claims that include the express language "means for" or "step for" be interpreted under 35 U.S.C. §112, paragraph 6. Claims that do not expressly include the phrase "means for" or "step for" are not to be interpreted under 35 U.S.C. §112, paragraph 6.

A portion of the present invention of this patent document contains material which is subject to copyright protection. The copyright owner has no objection to the facsimile reproduction by anyone of the patent document or the patent invention, as it appears in the Patent and Trademark Office patent file or records, but otherwise reserves all copyright rights whatsoever.

SEQUENCE LISTING

<160> NUMBER OF SEQ ID NOS: 6

<210> SEQ ID NO 1
<211> LENGTH: 45
<212> TYPE: PRT
<213> ORGANISM: Homo sapiens

```
<220> FEATURE:
<223> OTHER INFORMATION: Human beta-defensin-3 (hereinafter referred to
      as hBD-3)

<400> SEQUENCE: 1

Gly Ile Ile Asn Thr Leu Gln Lys Tyr Tyr Cys Arg Val Arg Gly Gly
1               5                   10                  15

Arg Cys Ala Val Leu Ser Cys Leu Pro Lys Glu Glu Gln Ile Gly Lys
            20                  25                  30

Cys Ser Thr Arg Gly Arg Lys Cys Cys Arg Arg Lys Lys
        35                  40                  45

<210> SEQ ID NO 2
<211> LENGTH: 10
<212> TYPE: PRT
<213> ORGANISM: Artificial Sequence
<220> FEATURE:
<223> OTHER INFORMATION: Fragment based on C-terminal region of hBD-3
      Cys5 and Cys6 of the last 10 residues of hBD-3 replaced with Ser

<400> SEQUENCE: 2

Arg Gly Arg Lys Ser Ser Arg Arg Lys Lys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Fragment based on C-terminal region of hBD-3
      Lys4 of the last 10 residues of hBD-3 replaced with Arg
      Cys5 and Cys6 of the last 10 residues of hBD-3 replaced with Ser

<400> SEQUENCE: 3

Arg Gly Arg Arg Ser Ser Arg Arg Lys Lys
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Fragment based on C-terminal region of hBD-3
      Last 10 residues of hBD-3

<400> SEQUENCE: 4

Arg Gly Arg Lys Cys Cys Arg Arg Lys Lys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Fragment based on C-terminal region of hBD-3
      Cys5 and Cys6 of the last 10 residues of hBD-3 replaced with Ser
      C-terminal amide at Lys10 of the last 10 residues of hBD-3
<220> FEATURE:
<221> NAME/KEY: AMIDATION
<222> LOCATION: 10

<400> SEQUENCE: 5

Arg Gly Arg Lys Ser Ser Arg Arg Lys Lys
1               5                   10
```

```
<210> SEQ ID NO 6
<211> LENGTH: 10
<212> TYPE: PRT
<213> ORGANISM: Artificial Sequence
<220> FEATURE:
<223> OTHER INFORMATION: Fragment based on C-terminal region of hBD-3
      Lys4 of the last 10 residues of hBD-3 replaced with Arg
      Cys5 and Cys6 of the last 10 residues of hBD-3 replaced with Ser
      C-terminal amide at Lys10 the last 10 residues of hBD-3
<220> FEATURE:
<221> NAME/KEY: AMIDATION
<222> LOCATION: 10

<400> SEQUENCE: 6

Arg Gly Arg Arg Ser Ser Arg Arg Lys Lys
1               5                   10
```

What is claimed is:

1. A cationic antimicrobial peptide (CAMP) conjugate comprising a CAMP conjugated to an antimicrobial agent, wherein the CAMP:
   a. comprises the amino acid sequence RGRRSSRRKK (SEQ ID NO: 3);
   b. is connected to the antimicrobial agent directly or through a linker segment, the antimicrobial agent being connected to the CAMP or the linker segment through a stable or cleavable bond; and
   c. carries and facilitates the delivery of the conjugated antimicrobial agent to a microbe.

2. The cationic antimicrobial peptide conjugate according to claim 1, wherein the CAMP comprises an amide group located on the C-terminus.

3. The cationic antimicrobial peptide conjugate according to claim 1, wherein the linker segment affixes the antimicrobial agent to the CAMP through acylation of the amino group of the N-terminus of the CAMP.

4. The cationic antimicrobial peptide conjugate according to claim 1, wherein the antimicrobial agent is levofloxacin.

5. The cationic antimicrobial peptide conjugate according to claim 1, wherein the antimicrobial agent is chloramphenicol.

6. The cationic antimicrobial peptide conjugate according to claim 1, wherein the antimicrobial agent is a diazeniumdiolate.

7. A method of producing a cationic antimicrobial peptide conjugate (CAMP) comprising:
   a. identifying a suitable carrier CAMP comprising the amino acid sequence RGRRSSRRKK (SEQ ID NO: 3);
   b. identifying a suitable antimicrobial agent; and
   c. creating a conjugate by conjugating the CAMP of step a with the antimicrobial agent of step b, wherein the CAMP:
      i. comprises the amino acid sequence RGRRSSRRKK (SEQ ID NO: 3);
      ii. is connected to the antimicrobial agent directly or through a linker segment, the antimicrobial agent being connected to the CAMP or the linker segment through a stable or cleavable bond; and
      iii. carries and facilitates the delivery of the conjugated antimicrobial agent to a microbe.

8. The method according to claim 7, wherein the CAMP comprises an amide group located on the C-terminus.

9. The method according to claim 7, wherein the linker segment affixes the antimicrobial agent to the CAMP through acylation of the amino group of the N-terminus of the CAMP.

10. The method according to claim 7, wherein the antimicrobial agent is levofloxacin.

11. The method according to claim 7, wherein the antimicrobial agent is chloramphenicol.

12. The method according to claim 7, wherein the antimicrobial agent is a diazeniumdiolate.

13. The cationic antimicrobial peptide conjugate according to claim 1, wherein the linker connects the antimicrobial agent to the CAMP via an amide bond between a carboxyl group of the linker and a side chain of a lysine residue of the CAMP.

14. The cationic antimicrobial peptide conjugate according to claim 1, wherein the antimicrobial agent or the linker is attached to the CAMP via an amide bond formed with a primary amino group of at least one of the N-terminus of the CAMP and a lysine side chain of the CAMP.

15. The cationic antimicrobial peptide conjugate according to claim 1, wherein the CAMP carries and facilitates the delivery of more than one of the conjugated antimicrobial agent to the microbe.

16. The method according to claim 7, comprising conjugating the antimicrobial agent to the CAMP via an amide bond between a carboxyl group of the linker and a side chain of a lysine residue of the CAMP.

17. The method of claim 7, comprising conjugating the antimicrobial agent or the linker to the CAMP through an amide bond formed between a carboxyl group of the antimicrobial agent or the linker and a primary amino group of at least one of the N-terminus of the CAMP and a lysine side chain of the CAMP.

18. The method according to claim 7, wherein the CAMP carries and facilitates the delivery of more than one of the conjugated antimicrobial agent to the microbe.

* * * * *